United States Patent [19]

Crescenti

[11] Patent Number: 5,698,583
[45] Date of Patent: Dec. 16, 1997

[54] OLIGOELEMENTS AND PHOSPHOLIPASE A2 IMMUNO-ENHANCER COMPOSITIONS, PREPARATION THEREOF, AND USE THEREOF

[76] Inventor: Ernesto J.V. Crescenti, Santander 556,, 1424, Buenos Aires, Argentina

[21] Appl. No.: 339,747

[22] Filed: Nov. 15, 1994

[51] Int. Cl.$^6$ .......................... A61K 51/00; A61M 36/14
[52] U.S. Cl. .......................... 424/1.11; 424/1.65; 424/400
[58] Field of Search .................... 530/300, 352, 530/350; 424/1.61, 1.65, 1.41, 1.45, 1.11, 9.1, 400; 435/183

[56] References Cited

U.S. PATENT DOCUMENTS

| | | |
|---|---|---|
| 5,112,864 | 5/1992 | Djuric et al. |
| 5,124,334 | 6/1992 | Wilkerson |
| 5,278,064 | 1/1994 | Berry et al. |
| 5,322,776 | 6/1994 | Knopf et al. |
| 5,350,579 | 9/1994 | Berry et al. |
| 5,354,677 | 10/1994 | Knopf et al. |

OTHER PUBLICATIONS

Rehm and Betz The Journal of Biological Chemistry, vol. 257, No. 17, issue of Sep. 10, pp. 10015–10022, 1982 "Binding of B–Bungarotoxin to Synaptic Membrane Fractions of Chick Brain".

Chang et al. Nauyn –Schmiedeberg's Arch Pharmacol., vol. 299, pp. 155–161, 1971. "Effects of $Sr^{2+}$ and $Mg^{2+}$ on Phospkolipose A and the Presynaptic Neuromuscular Blocking Actions of B–Bungarotoxin, Crotoxin, and Taipoxin".

Wells. Biochemistry, vol. II, No. 6, pp. 1030–1041. "A Kinetic Study of the Phospholipase $A_2$ (*Crotalus adamanteus*) Catalyzed Hydrolysis of 1,2–dibutyryl–sn–glycero–3–phosphorylcholine".

Holum. Elements of General, Organic, and Biological Chemistry, 9th Edition, pp. 42–47, "Periodic Law and Periodic Table".

*Primary Examiner*—John Kight
*Assistant Examiner*—Dameron L. Jones
*Attorney, Agent, or Firm*—Karen Lee Orzechowski; Nath & Associates

[57] ABSTRACT

An immuno-enhancer composition of at least one oligoelement selected from the group consisting of sodium selenite, magnesium chloride, manganese chloride, zinc chloride, cobalt, cerium, molybdenum, and silicon; and phospholipase A2. The preparation of the oligoelement and phospholipase A2 composition and its use in immunotherapy, treatment of oncologic diseases and degenerative diseases.

2 Claims, 18 Drawing Sheets

OLIGOELEMENTS AND PHOSPHOLIPASE A2 IMMUNO-ENHANCER COMPOSITIONS, PREPARATION THEREOF, AND USE THEREOF

FIELD OF THE INVENTION

The present invention is directed to a composition of oligoelements and phospholipase A2 for use as an immuno-enhancer and for the treatment of oncologic and degenerative diseases; the method of preparation of the oligoelement and phospholipase A2 compositions; and the use of the oligoelements and phospholipase A2 composition as an immuno-enhancer or in the treatment of oncologic and degenerative diseases.

BACKGROUND OF THE INVENTION

The therapeutic approach to cancer patients with advanced disease becomes very challenging when general condition (age, nutritional state, psychological attitude towards disease, availability of resources) rules out an appropriate therapeutic schedule. It becomes specially difficult in patients with multiple, non-surgical liver metastases who had undergone previous colonic surgery and for who radiotherapy is also out of question. It is in these cases that we were compelled to employ non-traditional therapeutic methods which may be classified as immunotherapy.

In this wide field there are multiple approaches in different stages of investigation, from the use of BCG in the treatment of melanoma with diverse success (13,14), to the recent administration of lymphocytes obtained from the patient's tumor replicated in culture with interleukin 2 (IL2), after a single dose of cyclophosphamide, with transient remissions (15). The activation of T killer lymphocytes (LAK) with a single dose of mytomyicin C apparently diminishes $CD_8$ suppresser levels, but although both factors promote antitumoral immunity, the method is complex and the results obtained are poor (16). In the same theoretical path is the use of LAK activated by IL 2 in the treatment of lung and liver metastases originating from animal tumors (17,18). Similarly, the administration of anti CD3 antibodies, that enhances the patient's cellular immunity through the modification of the helper/suppressor ratio, should have an antitumoral effect (19). On the other hand, the well known therapeutic use of α interferon in hairy cell leukemia has been extended to the treatment of chronic myelogenous leukemia (21), kidney carcinoma (22,23), non-Hodgkin lymphomas (24,25,26), multiple myeloma (27) and melanoma (28), invariably as a palliative agent. Nevertheless, it is not indicated, even as a palliative method in liver metastases of colonic carcinomas and at the time we began with this study, neither Interferon were available in our country.

SUMMARY OF THE INVENTION

In the critical situation of providing merely a symptomatic treatment, waiting for the unavoidable end, the possibility of employing a non-traditional method of immune stimulation. The treatment originally consisted in the administration of mineral and plant extracts, associated to an $A_2$ phospholipase, in very low doses. Our investigations led us to replace the extracts by the active principles present, namely, different oligoelements identified as zinc (Zn), selenium (Se) and manganese (Mn), which have been shown to exert antimmoral activity. For instance, selenium has been widely recommended as a preventive in neoplasic disease because of its antioxidant effect, which antagonizes the action of carcinogens (29). It has also been demonstrated that selenium inhibits specific phosphodiesterases with the subsequent increase in cAMP levels (30).

Zinc plays a critical role in the synthesis of various serum proteins like albumin, pre albumin and transferrin and its deficiency may modify the immune response (31).

Manganese belongs to the group of essential oligoelements recommended by the American Medical Association for the intravenous nutrition of oncological patients (31,32, 33).

The inclusion of $A_2$ phospholipase in the therapeutic combination, was based on the mechanism of action of the Tumor Necrosis Factor (TNF). Since 1984 it has been recognized that monocytes and macrophages acquire the capacity of destroying neoplasic but not normal cells in co-culture, when they are activated by lymphokines. This method cannot be applied in vivo because of the extremely short half life of γ interferon when administered intravenously, so that for successful activation, a minimum of eight hours of interaction with macrophages is required (35). This action was mediated by a substance formerly called lymphotoxin and the minor necrosis serum (TNS). To enable this effect, the presence of lysosomes and of a membrane-associated phospholipase $A_2$ activity were required, preceded by raised calcium levels in target cells (36,37). Later, it was demonstrated that TNF acts through the activation of $A_2$ phospholipase; an enzyme wich catalyzes the cleavage of the sn-2-acyl bond of phospholipids with the subsequent mobilization of arachidonic acid serving as a critical step in the biosynthesis of eicosanoids (38,39).

In this study, we present the results of long-term follow up of 21 patients with metastatic colon adenocarcinoma who received the combined treatment with oligoelements and phospholipase, at very low doses. The therapeutic doses employed were determined from previous investigations performed with rumor cells cultured in vitro and from the in vivo treatment of animals with chemically induced experimental carcinomas (12).

DETAILED DESCRIPTION OF THE INVENTION

Figure 1:
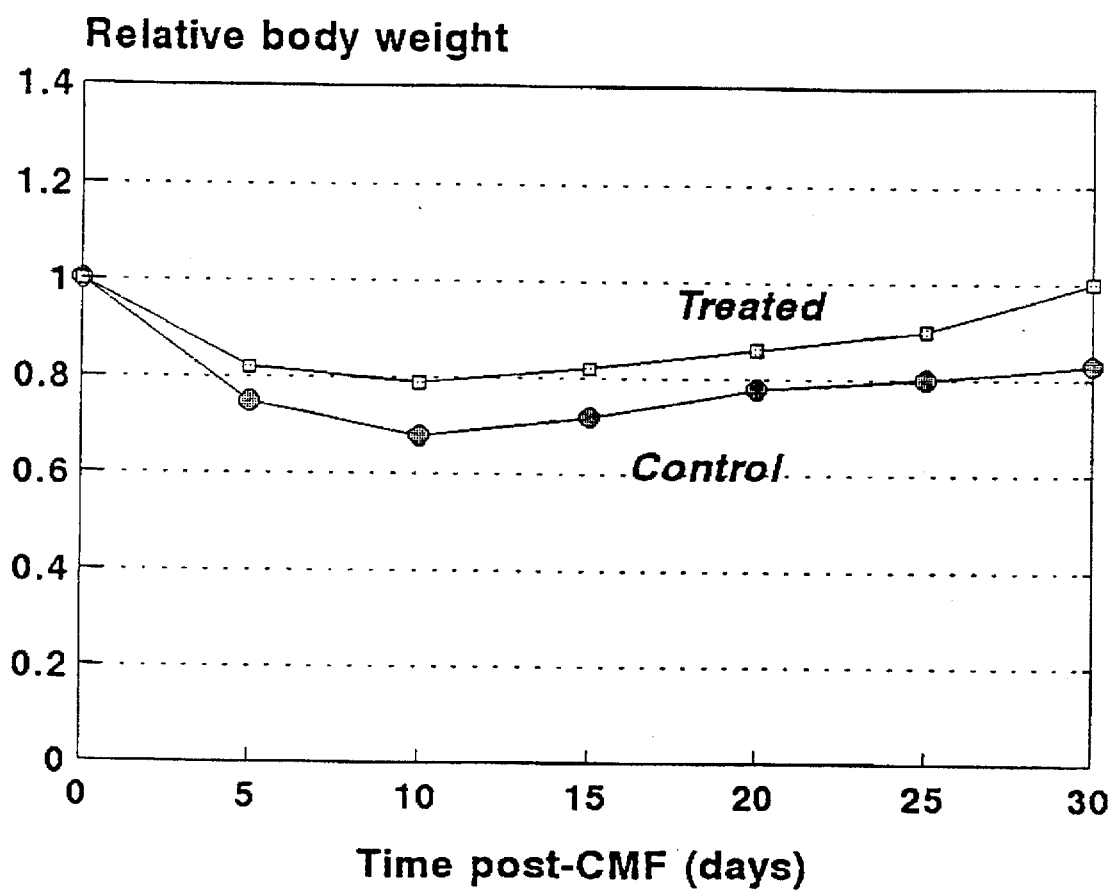
FIG. 1. Mean relative body weight variation in rats treated with 12-fold CMF (12 times the basic dose of cyclophosphamide 500 mg/m$^2$, methotrexate 40 mg/m$^2$ and 5-fluoracil 600 mg/m$^2$) alone versus those also protected with micronutrients Mn-Se-Zn plus $PLA_2$, highlighting that in the protected group the decrease in body weight was milder and recovery is faster.
Figure 2:
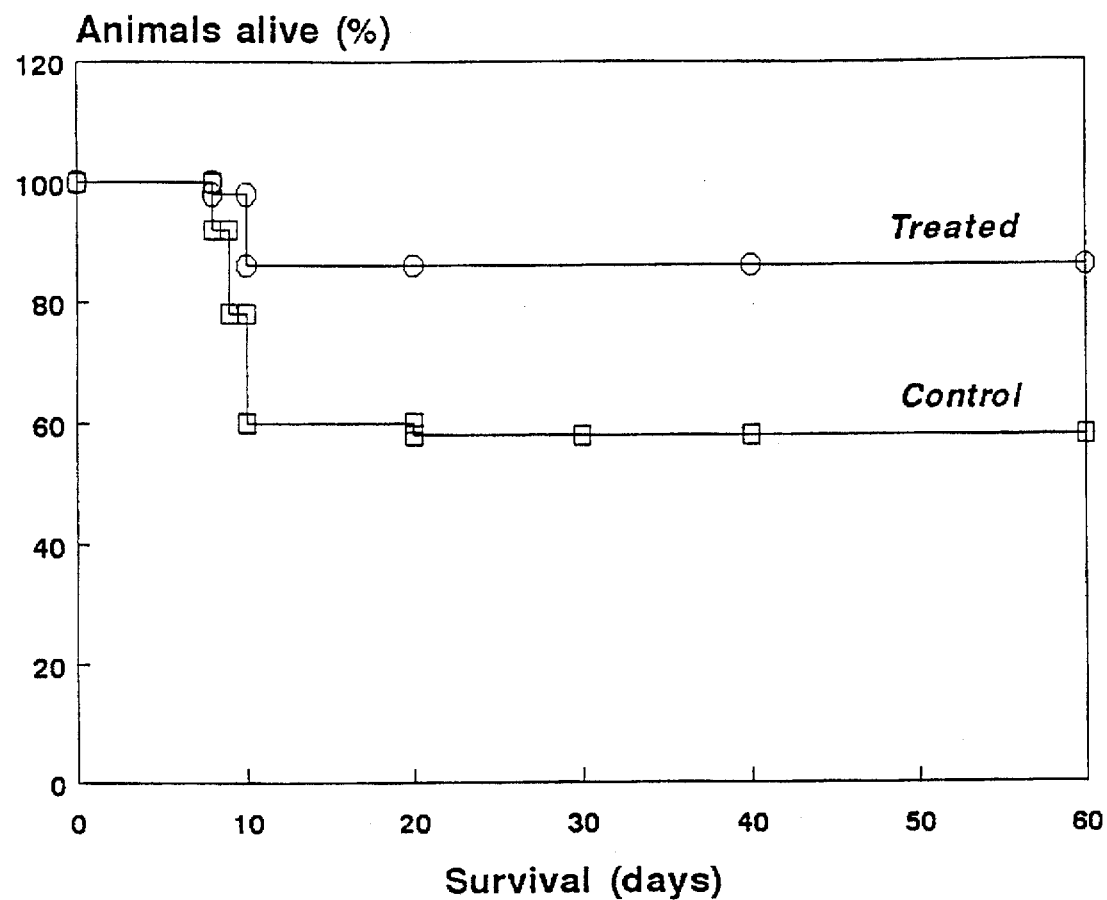
FIG. 2. Data represent global survival percentages of the various batches of control and OP-protected rats, up to 60 days post-CMF treatment ranging from 4- to 20-fold the basic dose (cyclophosphamide 500 mg/m$^2$, methotrexate 40 mg/m$^2$ and 5-fluororacil 600 mg/m$^2$).

The application of antioncological drugs in human patients has enabled great progress to be made in the treatment of common malignant tumors such as breast, colon and lung carcinoma [1,2,3,4,5]. However, results are as yet limited. One of the main drawbacks is the incomplete destruction of micrometastases not removable at primary surgery. It has been shown that when masses of atypical cells undergoing the avascular growth phase reach 150 to 500 µm in diameter [6], they present a decrease in the diffusion of nutrient or toxic components towards the center of microspherules. During this phase central cells are still viable and enhance with tritiated thymidine; in contrast, radiolabelled chemotherapeutic drugs such as methotrexate [7] fail to reach the core of the lesion. Thus, the diffusion gradient becomes a limiting factor so that greater active drug concentration is required in the intercellular space. It is precisely at this point where the main limitation of chemotherapy appears, as its toxic effects on bone marrow, kidney, digestive mucosa and liver prevent indiscriminate application.

Progress has been achieved in the application of massive doses with the help of hematopoietic stimulating factors (G-CSF and GM-CSF) which allow bone marrow recovery following high-dose chemotherapy [8,9,10]. Despite this accomplishment, barely 5,000 mg/m$^2$ of cyclophosphamide can be administered, which is equivalent to 6 or 7 times the usual dose [8,9,10], with some decrease in bone marrow toxicity.

In the present study, doses were raised to 10 or 15 times the habitual level of the three associated drugs, by means of a procedure which does not alter the efficacy of the drugs on atypical cells and protects all affected organs. The chemotherapeutic combination chosen for this purpose was cyclophosphamide, methotrexate and 5-fluoruroacil (CMF).

On the basis of data gleaned from the literature, neither oligoelements nor phospholipases have been considered to modify significantly the action of chemotherapeutic drugs on atypical cells [11–14]. To illustrate, selenium (Se) has been reported incapable of producing in vitro protection of atypical fibrosarcoma cells against antineoplasic drugs [13]. Likewise, Tobey's work [15,16] on zinc (Zn) and Se show that the in vitro protective effect on normal cells is not significant in the case of neoplasic cells.

CMF doses of 500 mg/m$^2$, 40 mg/m$^2$ and 600 mg/m$^2$, respectively, are regarded as habitual. As already stated, these drugs were chosen for being the most commonly employed association for human breast cancer [1,2,17,18, 19].

As protective elements for normal cells, the oligoelements Zn, Se and Mn were used on the basis of plentiful data. For instance, in the case of Zn alone, its protective in vitro function against the effect of alkylating agents in cell cultures [15,16] enabled the application of 10 times the chemotherapeutic dose in pretreated versus non-pretreated cultures, and up to 16 times such dose {when} associated with Se and Cu. The mechanism of action would appear independent of metallothionein synthesis, a protein capturing heavy metals [16], which has been demonstrated for the protection afforded by pre-treatment with Zn prior to cisplatin application [11,20]. In the case of alkylating agents, Zn acts through an increase in glutathion content and glutathion-S-transferase activity [20]. It has been observed that weight loss induced by cyclophosphamide in rats may be reversed by addition of cysteine employed to produce glutathion [12,20]. Likewise, hemorrhagic cystiris caused by acroleine (a cyclophosphamide metabolite) is also inhibited by injection of cysteine and glutathion [21]. These same components are employed to prevent cyclophosphamide teratogenesis in pregnant rats [22]. However, the therapeutic efficacy of the drug remains unaltered by such protective effects [12,21].

As regards methotrexate, Zn-stimulated glutathion action is associated to transport of the drug within cells [23]. Se also exerts an effect on glutathion metabolism by increasing the enzymatic activity of Se-dependent glutathion peroxidase [24,25,26], which prevents the effects of carcinogens and of alkylating agents. Interestingly, such enzymatic increase takes place selectively in certain organs (kidney, colon mucosa and small bowel), which may explain the prevention of toxicity in certain tissues [27], a finding confirmed by the reduction in renal toxicity of cis-platin exerted by Se [13].

Besides, it has been shown that less DNA chain fractures are induced by carcinogens following Se pre-treatment [28].

Both Zn and Se are able to inhibit carcinogenesis secondary to antineoplasic drugs employed in human patients and to the most common carcinogens used in experimental animals [13,16,24,25,26,29–31].

For its part, Mn acts as a superoxide dismutase catalyst in the prevention of cell damage induced by oxidizing agents, particularly the superoxide ion [32,33].

It has been demonstrated that glutathion depletion due to gamma-glutamyl cysteine synthetase inhibition blocks the production of gamma-interferon secreting cells by roughly 80% [34]. The prevention of this process by means of Zn and of Se may help to improve the immune response in animals under treatment with alkylating agents.

The inclusion of phospholipase $A_2$ in our schedule was due to the fact that it makes up the association originally used with success for the control of experimental rat mammary tumors induced by N-nitroso-methylurea [35].

Studies carried out in our laboratory show that the combination of oligoelements, Zn, Se and Mn, plus phospholipase $A_2$ (OP) has a satisfactory effect on Sprague-Dawley rats with experimentally induced mammary tumors, achieving prolonged survival, improvement in general status, decrease in tumor size and body weight increase [35].

On the basis of the foregoing background, in vivo tolerance studies were performed in Sprague-Dawley rats to systemic treatment with the CMF combination, by administering continuous OP medication starting one month prior to the application of various CMF dose schedules.

SOLUTION PREPARATION

Materials and Methods

Chemicals

Sodium selenite, Magnesium chloride, Manganese chloride, Zinc chloride, Cobalt powder, Cerium powder, Molibden powder and Silicon powder are drugs of analytical grade and purchased from Aldrich Chemical Co., USA. Phospholipase A2 is a purified fraction from venom of Crotalus Dussirus Terrorificus and from Lachesis Muta.

Preparation of the stock solutions

Oligoelements

In a first step, stock solutions of each oligoelement are prepared in distilled water. The concentration of these solutions is $4 \times 10^{-3}$ g/ml. Salts are directly dissolved in distilled water; powders are previously treated as follows:

Silicon: 50 ml of NaOH (10% w/v) are added to 4 gr. of powder with continuous stirring at 100° C., during 30 minutes. Complete dissolution is obtained after 15 to 20 hs at room temperature. The solution is filtered and distilled water is added to complete a final volume of 1 liter.

Molybdenum: 100 ml of $NO_3H$ (10% v/v) are added carefully to 4 gr. of powder with continuous stirring at room temperature until complete dissolution. The solution is filtered and distilled water is added to complete a final volume of 1 liter.

Cobalt/Cerium; 100 ml of ClH (10% v/v) are added to 4 gr. of powder, with continuous stirring until complete dissolution. The solution is filtered and distilled water is added to complete a final volume of 1 liter.

Phospholipase $A_2$

The stock solution containing $10^{-4}$ g/ml of phospholipase A2 is prepared in 50 mM sodium phosphate buffer, pH 7. This solution is stored at −20° C.

Composition of the final solution

The final solution is prepared mixing aliquots from the different stock solutions of the oligoelements and adding distilled water in order to obtain a final concentration of $4 \times 10^{-6}$ g/ml for each component. The phospholipase $A_2$ is added to a final concentration of $4 \times 10^{-9}$ g/ml. The pH of the solution must be adjusted to 7.2–7.4 with phosphate buffer before adding the phospholipase.

Route of administration and doses 1 ml of the solution is administered daily by subcutaneous injection.

ANIMAL STUDIES

Materials and Methods

Eighteen batches of Sprague-Dawley strain rats were employed to determine the $LD_{50}$ of the most commonly employed combination for the treatment of human breast tumors, consisting of cyclophosphamide, methotrexate and 5-fluoruroacil (CMF). Once mortality curves had been traced, animal batches were given oligoelements (Se, Zn and Mn) plus phospholipase $A_2$, followed 15 days later by CMF administration. A clearcut significant shift towards the fight was observed in survival curves (P<0.001) with a CMF $LD_{50}$ dose equivalent to roughly 18,3 times the dose given to humans. All animals were necropsied at the time of death or when killed two months after CMF administration. Anatomopathological studies disclosed renal tubule lesions, hepatic centrolobular steatosis and diverse degrees of bone marrow aplasia. Rats not protected with oligoelements and phospholipase $A_2$ presented more severe lesions such as grade III bone marrow aplasia, greater incidence of massive sepsis, acute renal tubule necrosis and greater incidence of malignant tumors (37.5% of chronic myeloid leukemia). Protected survivors displayed ad integrum recovery from the described anatomopathological lesions. Such results afford the possibility of applying this treatment to human patients subjected to high-dose chemotherapy, in order to improve their tolerance.

Animals

Roughly 4-month-old male Sprague-Dawley rats, inbred in our laboratory and weighing 380–420 g at the start of the experiments, were used. Animals were kept in groups of 5 each per cage, with water and food ad libitum, temperature at 22°–23° C., humidity at roughly 56% and 12 hours light cycle. Body weight was monitored every other day.

Treatments

Throughout, batches of rats protected and unprotected with OP medication were available. Treatment with chemotherapeutic drugs (CMF): For tolerance studies, a combination of cyclophosphamide, methotrexate and 5-fluoracil (CMF), (the most commonly administered for human mammary carcinoma [1,2,17,18,19]), was given as a single dose. The lowest CMF dose (indicated as 2-fold) was calculated by extrapolating the double value of that used in human patients, namely, cyclophosphamide 500 mg/m$^2$, methotrexate 40 mg/m$^2$ and 5-fluoracil 600 mg/m$^2$. The range of doses employed were multiples of the latter and their expression was 4-, 10-, 12-, 14-, 16-, 18- and 20-fold, respectively. Cytostatic multidrug injections were delivered by intraperitoneal route.

Protection with oligoelements and phospholipase A$_2$ (OP): Each rat receiving OP protection was injected daily, starting 10 days before CMF administration; with a solution of oligoelements Zn, Se and Mn (0.15 μg/100 g body weight) and phospholipase A$_2$ (10 ng/100 g body weight), supplemented with phosphatidyl-inositol and phosphatidyl-choline in buffered vehicle, as described elsewhere [14,15]. The OP combination was administered concentrated in a 0.5-ml volume by subcutaneous route and 0.1 ml by oral route, during a maximum of 70 days.

Protection protocol: All batches consisted of 8 rats each, with a total of 128 animals. Batches 1, 3, 5, 7, 9, 11, 13 and 15 received 2-, 4-, 10-, 12-, 14-, 16-, 18- and 20-fold CMF, respectively, while batches 2, 4, 6, 8, 10, 12, 14 and 16 received OP medication starting 10 days earliest as indicated above, besides the given range (2- to 20-fold) of CMF doses.

Parameters recorded: The following studies were carried out on all batches: a) body weight monitoring (every other day); b) observation of collateral macroscopic effects including changes in fur coloration, hair loss and nasal and gut hemorrhage; c) LD$_{50}$ determination; and d) necropsy to determine the cause of death in every case and for histopathological study of organs and tissues.

Histopathological studies

All animals were autopsied at the time of spontaneous death or when killed 60 days after CMF administration. Viscerae block and the sixth dorsal vertebrae were removed and immediately fixed in 10% formaldehyde buffer. After careful macroscopic study, specimens of lung, liver, heart, kidney, spleen, genitalia and bone marrow were harvested for histological study. Tissues were imbedded in paraffin and stained with hematoxylin-eosin, Giemsa, periodic acid-Schiff (PAS) and other special techniques as required.

Statistical analysis

Survival curves for control and protected batches of rats, for each dose assayed, were fitted by the Kaplan-Meier method [36], then compared by means of the Mantel-Cox [37] and Wilcoxon [38] tests, to render compatible results throughout.

Effective LD$_{50}$ doses were estimated for both control and protected batches by the Litchfield-Wilcoxon method [39].

Histopathogical studies

Figure 8:
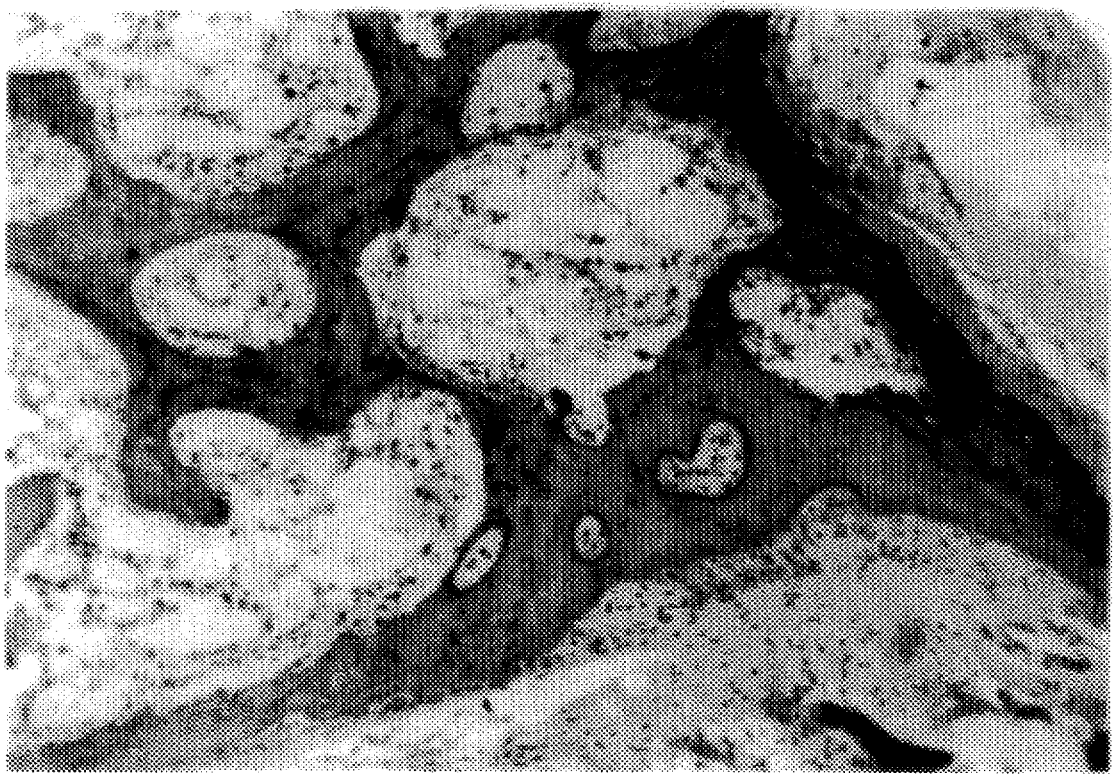
FIG. 8. Depletion of normal bone marrow progenies and replacement by adipose tissue in an unprotected rat treated with 14-fold CMF (basic dose: cyclophosphamide 500 m/m$^2$, methotrexate 40 m/m$^2$ and 5-fluoruracil 600 m/m$^2$) and found dead at 8 days. Aplasia grade III (H-E, 100 X).
Figure 9:
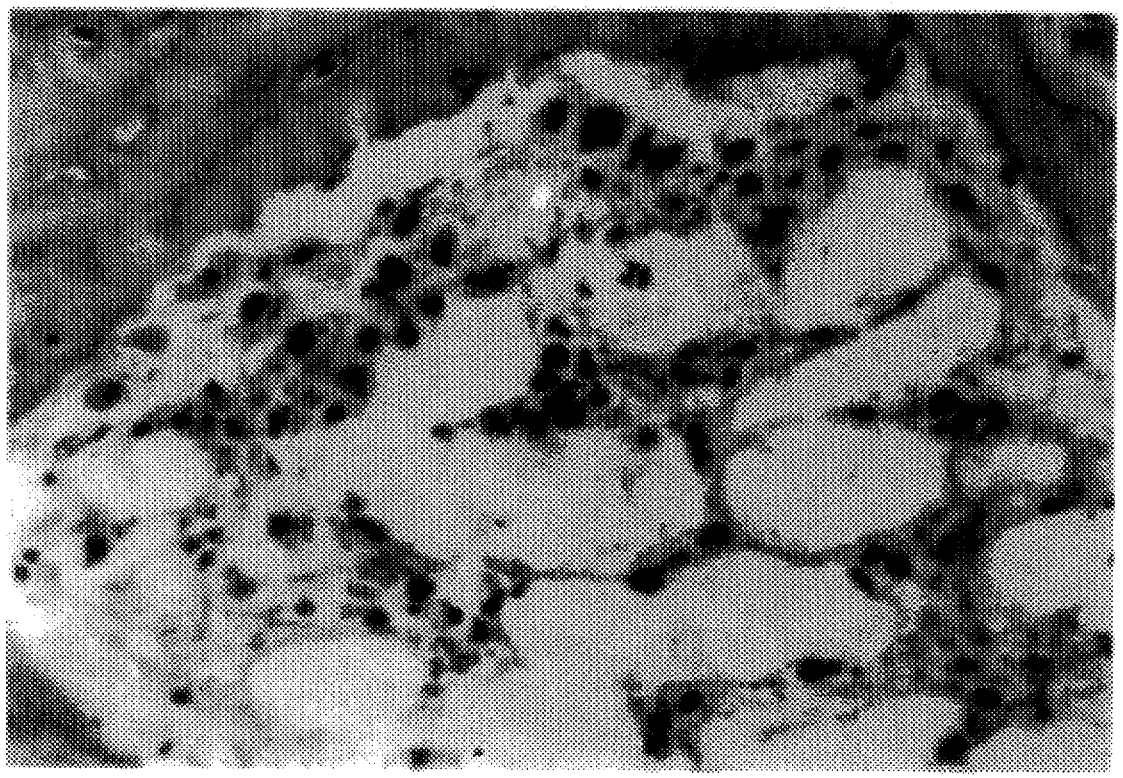
FIG. 9. Bone marrow with loss of hemopoietic components and persistence of lymphocytes, histiocytes and stroma cells in an unprotected rat found dead at 8 days receiving 14-fold CMF (cyclophosphamide 500 mg/m$^2$, methotrexate 40 mg/m$^2$ and 5-fluoruracil 600 mg/m$^2$). Aplasia grade III (H-E, 400 X).
Figure 10:
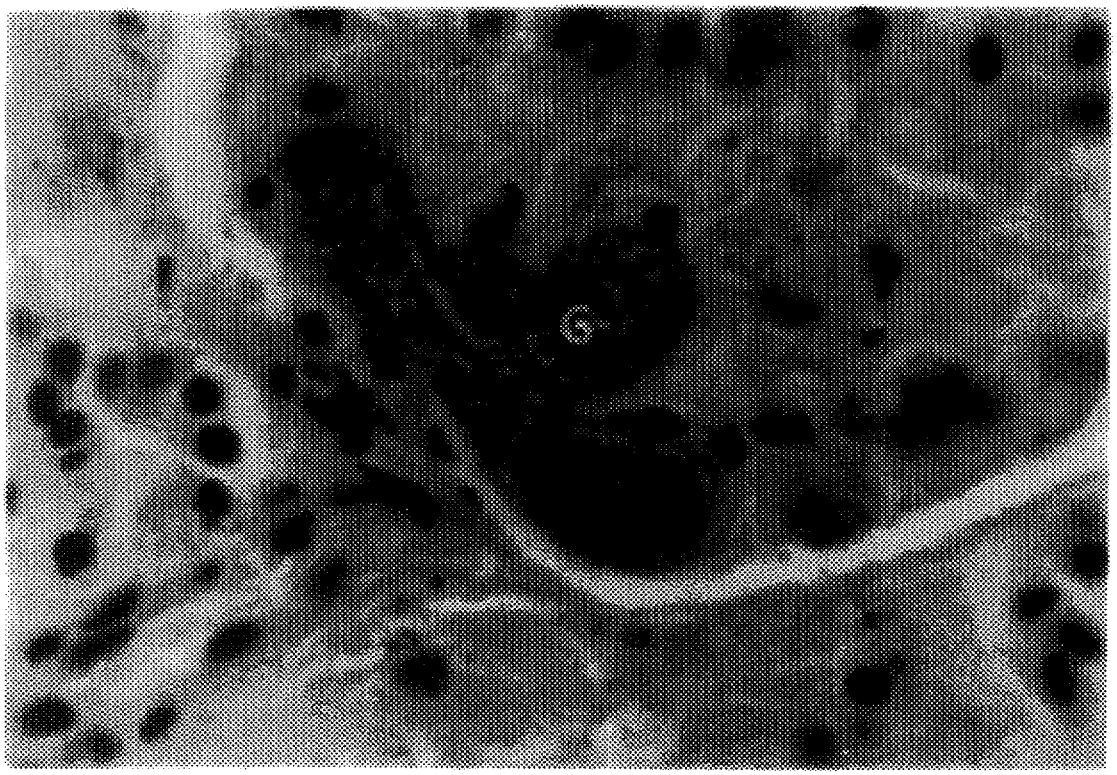
FIG. 10. Septic embolia in renal glomerular vessels in an unprotected rat found dead at 11 days receiving 10-fold CMF (basic dose: cyclophosphamide 500 m/m$^2$, methotrexate 40 mg/m$^2$ and 5-fluoruracil 600 mg/m$^2$) (H-E, 630 X).
Figure 11:
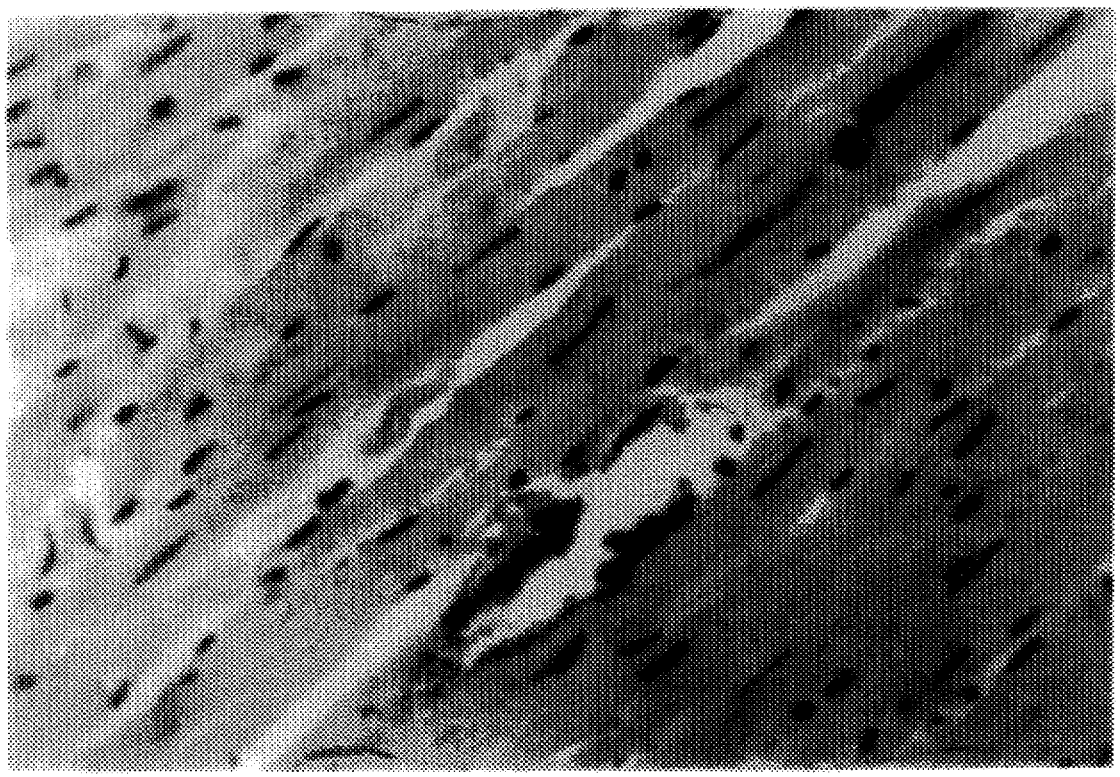
FIG. 11. Bacterial colonies in myocardium in an unprotected rat found dead at 10 days receiving 10-fold CMF (basic dose: cyclophosphamide 500 mg/m$^2$, methotrexate 40 mg/m$^2$ and 5-fluoruracil 600 mg/m$^2$) (H-E, 400 X).
Figure 12:
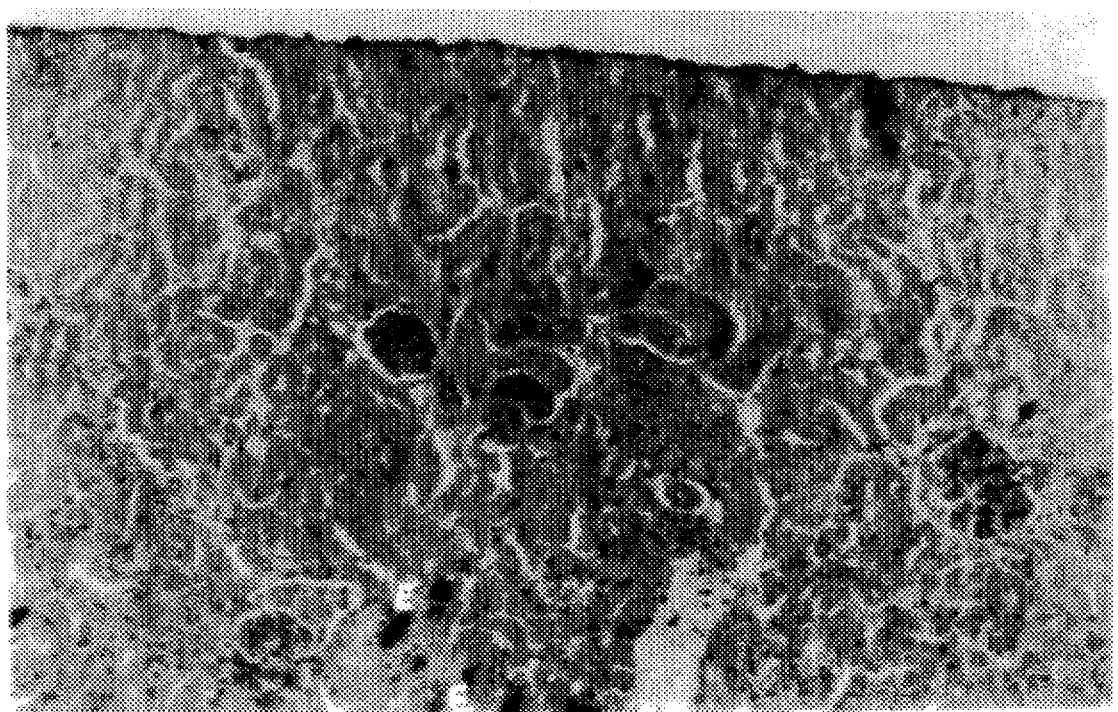
FIG. 12. Renal tubular necrosis with partial sparing of glomeruli and presence of septic embolia in an unprotected rat found dead at 7 days receiving 16-fold CMF (basic dose: cyclophosphamide 500 mg/m$^2$, methotrexate 40 mg/m$^2$ and 5-fluoruracil 600 mg/m$^2$) (H-E, 100 X).
Figure 13:
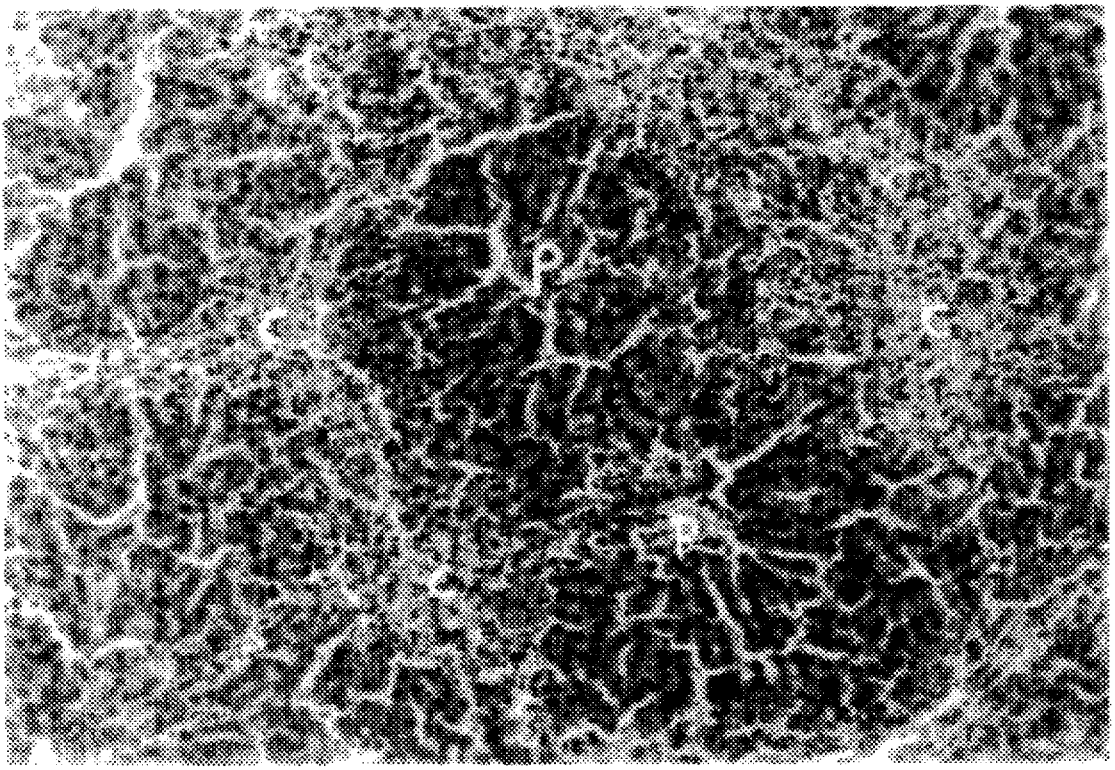
FIG. 13. Centrilobular areas with slight hepatocytic necrosis and lymphocytic infiltration in an unprotected rat found dead at 12 days receiving 18-fold CMF (basic dose: cyclophosphamide 500 mg/m$^2$, methotrexate 40 mg/m$^2$ and 5-fluoruracil 600 mg/m$^2$). Portal areas are spared (H-E, 100 X).

Anatomopathological lesions found mainly involved bone marrow, kidney and, to a much lesser extent, liver. Besides, they differed remarkably according to the time of death. Thus, in rats unprotected found dead from 7 to 12 days (95% mortality) after administering CMF, the severity of bone marrow aplasia found in 100% ranged from grade II to III (FIGS. 8,9) and generalized acute sepsis with bacterial colonies was evident in one or more studied organs (80%) (FIGS. 10,11). While acute renal tubular necrosis (60%) (FIG. 12) and centrolobular hepatic lesions were relatively slight (40%) (FIG. 13).

A second group comprising 5% of unprotected rats died spontaneously after 25 days/at 13–25 days of CMF application. In this group anatomopathological lesions were scarce, without evidence of bone marrow aplasia, but with kidney lesions or sepsis in some cases.

Protected animals displayed differences in the cause of death versus the control group, which proved more noteworthy with certain critical CMF doses. At the 16-fold CMF dose, 80% of controls died of sepsis, whereas barely 20% of OP-protected rats in this group showed signs of sepsis. For the same dose, 80% of unprotected animals presented bone marrow aplasia, whereas only 10% of protected rats displayed this lesion at the time of death.

Figure 14:
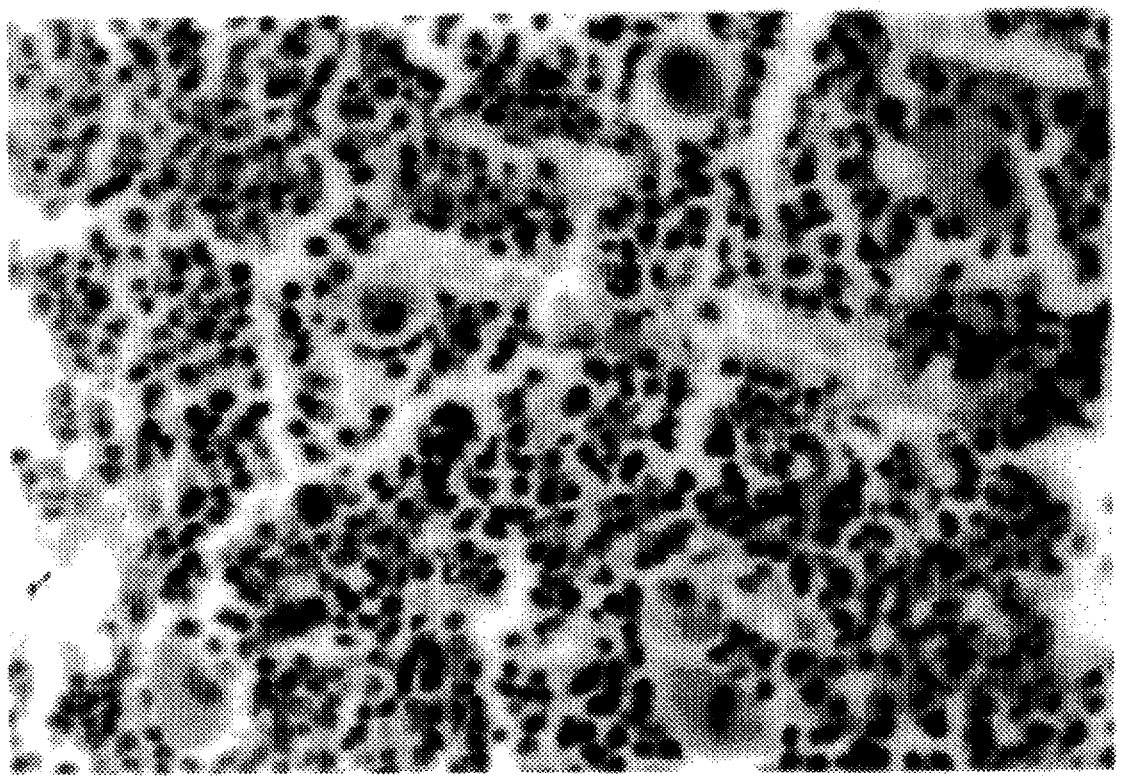
FIG. 14. Bone marrow with evident chronic myeloid leukemia infiltrates and disappearance of normal adipose tissue in an unprotected rat killed at 60 days post-CMF treatment and receiving 16-fold CMF (basic dose: cyclophosphamide 500 mg/m$^2$, methotrexate 40 mg/m$^2$ and 5-fluoruracil 600 mg/m$^2$) (H-E, 400 X).
Figure 15:
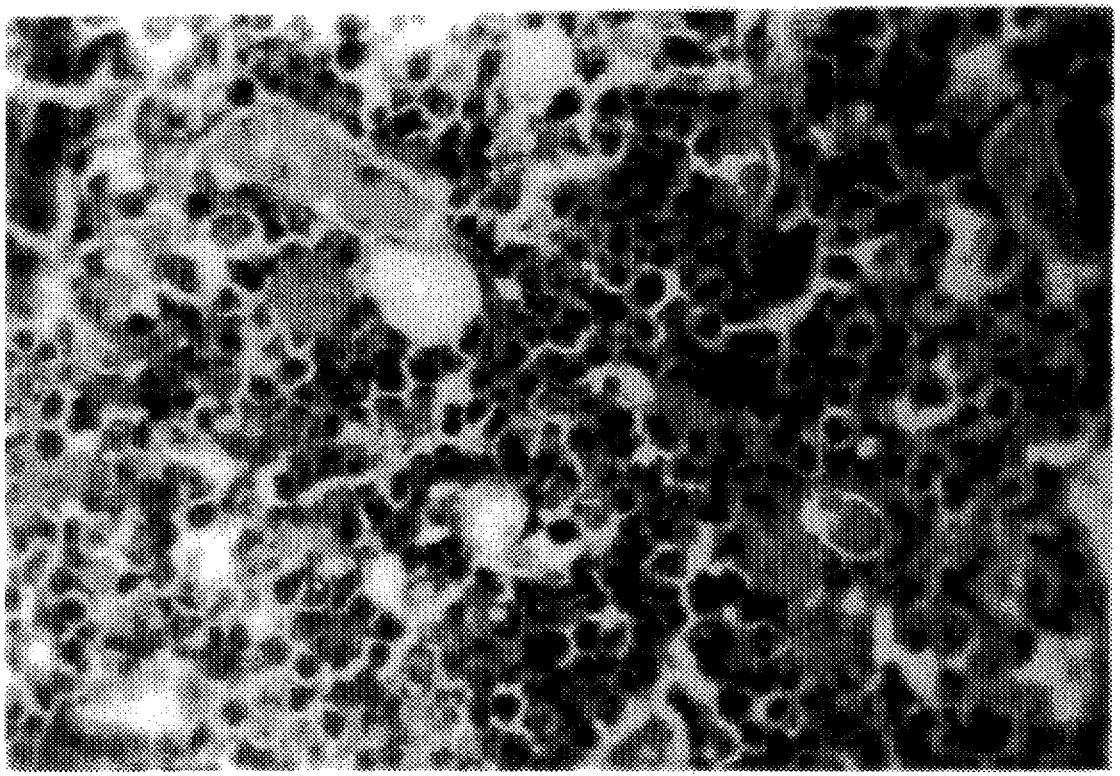
FIG. 15. Bone marrow with predominance of myeloid leukemia components including blastic forms in an unprotected rat killed at 60 days receiving 16-fold CMF (basic dose: cyclophosphamide 500 mg/m$^2$, methotrexate 40 mg/m$^2$ and 5-fluoruracil 600 mg/m$^2$) (H-E, 400 X).
Figure 16:
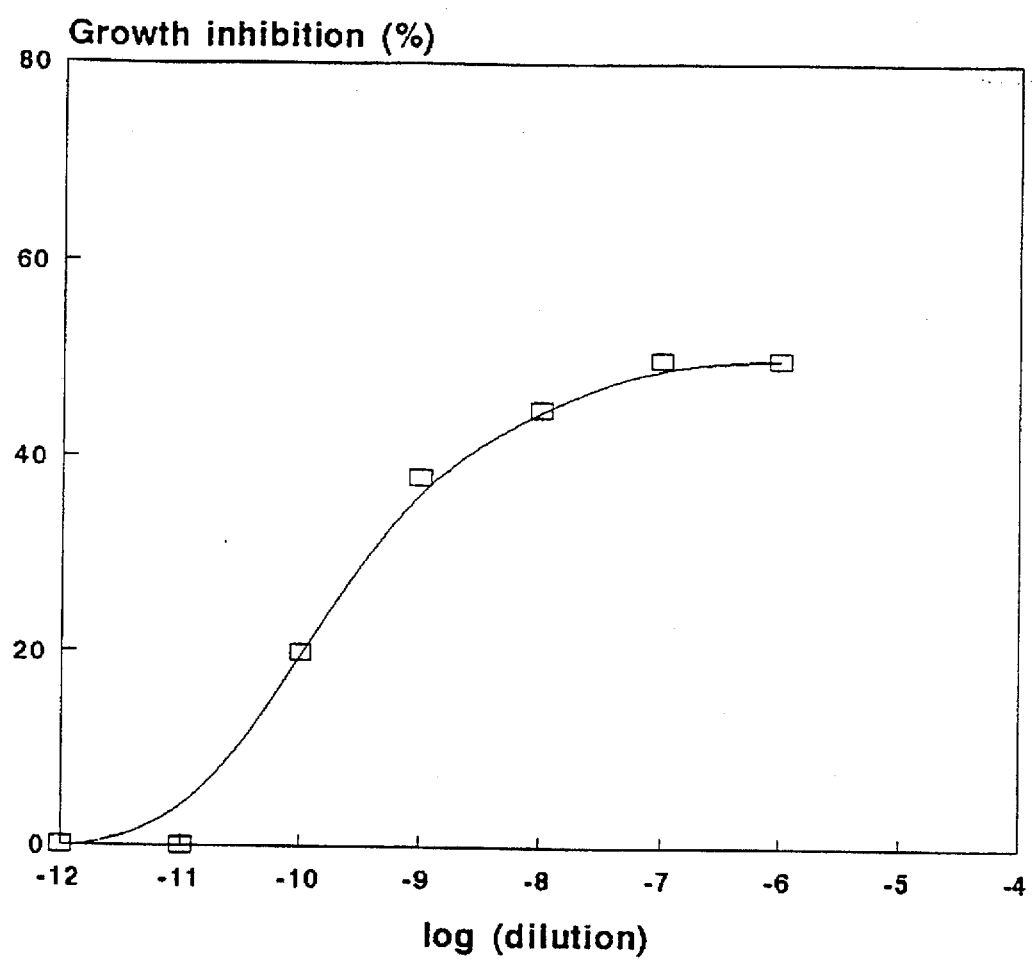
FIG. 16 Dose-response curve representing inhibition percentage (%) in the formation of colonies in soft agar for different dilutions of oligoelements. Doses are expressed as inverse log of the dilution of the main solution. Clonogenic techniques of colony formation in agar were employed as described in Materials and Methods.
Figure 17:
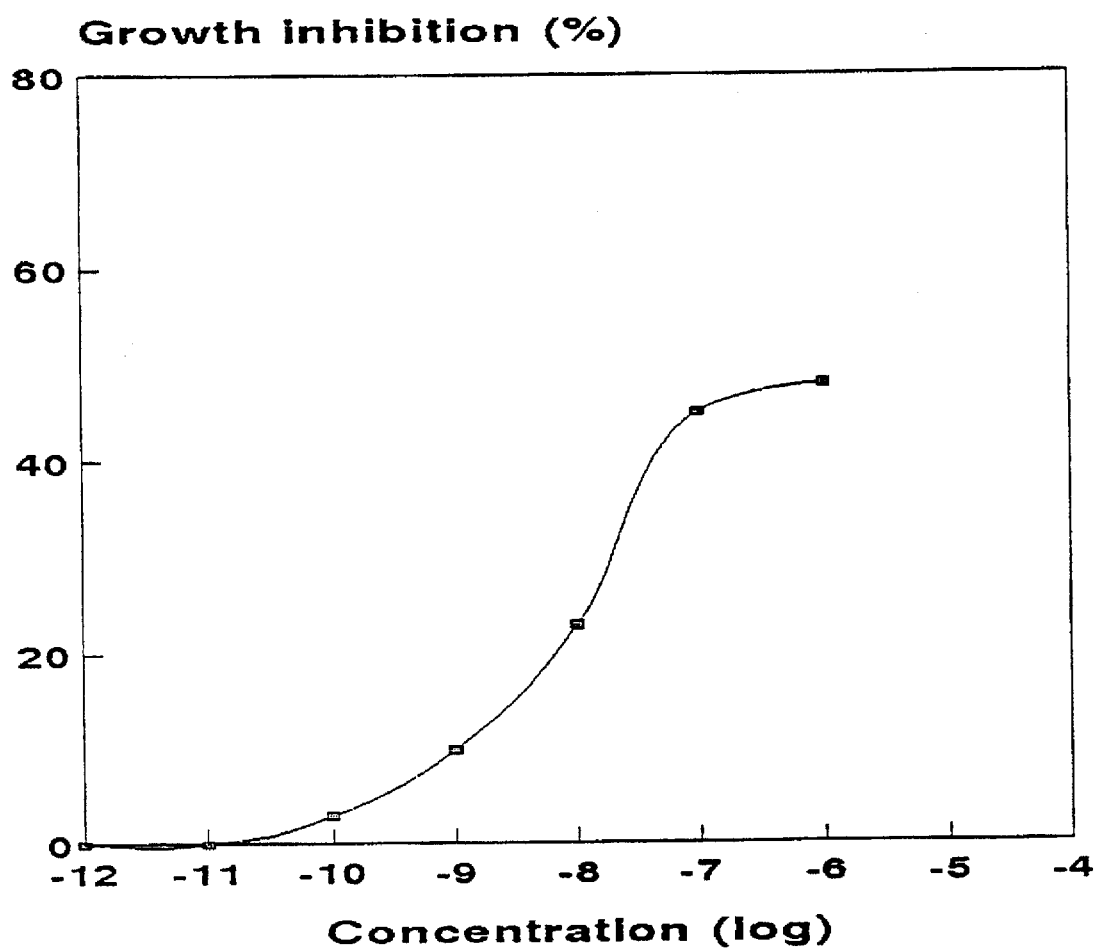
FIG. 17 Dose-response curve representing inhibition percentage (%) in the formation of colonies in soft agar for different dilutions of the combination of oligoelements plus phospholipase A2. Doses are expressed as log of the dilution of the main solution. Clonogenic techniques of colony formation in agar were employed as described in Materials and Methods.
Figure 18:
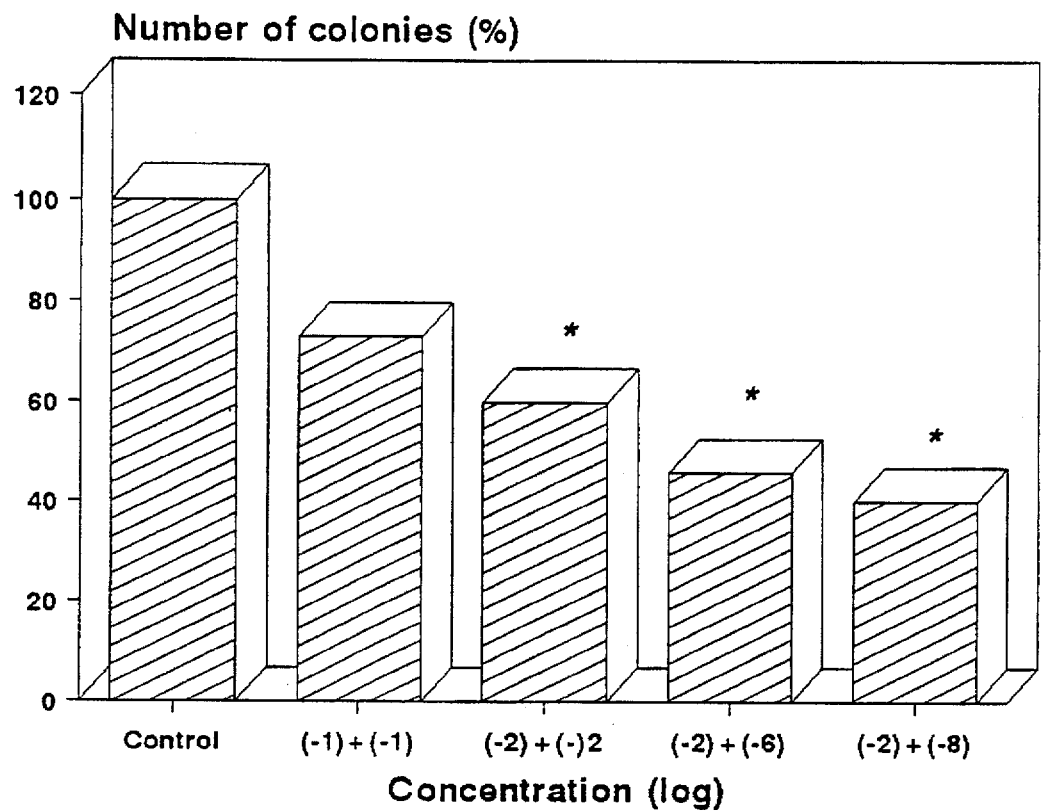
FIG. 18 Formation of colonies in soft agar for different combinations of phospholipase $A_2$. Dilutions of both components are expressed as log of the dilution of the main solution. For statistical purposes, a two-way ANOVA and Tuckey's test were applied.

In studies performed on survival animals killed at 60 days, practically all controls exhibited myeloid leukemia in bone marrow (FIGS. 14,15). In contrast, none of the protected rats did so, showing normocellular or slightly hypercellular bone marrows.

On the whole, in control groups failing to present aplasia at the time of death, a great percentage displayed chronic myeloid leukemia (FIG. 14), which in one case proved blastic in nature (FIG. 15). In contrast, none of the OP-protected rats in any group or for any dose presented leukemia.

On the basis of the foregoing studies, it was found that LD$_{50}$ for unprotected control rats was 14.1- fold the basic one versus 18.3-fold for OP-protected animals, indicating a great shift in tolerance to cytostatic treatment which would enable therapeutical doses to be raised with a satisfactory safety margin. Recalling that a 14-fold dose failed to cause deaths in protected groups in contrast to 50% mortality in controls, the basal dose might well be increased 2- or 3-fold without appreciable danger. Furthermore, with the 16-fold dose mortality was 20% in OP-protected batches, where 80% of deaths were due to hemorrhage related to bone marrow alterations and associated to acute renal tubular necrosis, collateral effects liable to be controlled in humans by transfusion of platelets and clotting factors. It is worthwhile stressing the two chronological phases of spontaneous death by chemotherapy in rats not protected with OP. The first phase was around 10 days and due to sepsis in 80% of cases, associated almost invariably to acute renal tubular necrosis and bone marrow aplasia: barely 20% of unprotected animals died of acute renal tubular necrosis or bone marrow aplasia, remaining free of sepsis. A second phase of deaths was discernible at 15–25 days, due to causes poorly evidenced morphologically, but most likely of a central circulatory nature (cardiac, of large vessels or circulatory function), with a recovered bone marrow on occasion hyperplasic, splenic myelopoiesis and frequent chronic myeloid leukemia in bone marrow. A certain degree of chronic metabolic failure, whether hepatic or renal, cannot be ruled out during this second stage.

In OP-protected animals, death due to generalized sepsis at 8–12 days decreased drastically from 80 to 20%, and mortality was mainly attributable to acute renal tubular necrosis and bone marrow aplasia during this first phase. Such finding strengthens the hypothesis of an immunostimulating action exerted by the oligoelements, already described in the literature [34,40] and which the present authors have reported for the treatment of experimentally-induced rat tumors [35].

In protected animals, no deaths were recorded in the second phase thats its 25 days post-CMF.

At the time of spontaneous death or when killed, unprotected control rats invariably presented either of two bone marrow pathologies: bone marrow aplasia in the earlier phase or chronic myeloid leukemia, at times biastic in nature, in the later phase. In contrast, there were no cases of myeloid leukemia in treated groups, thus demonstrating the protective effect of OP medication against the carcinogenic action of the chemotherapeutic agents employed. Such beneficial effect seems mainly attributable to selenium and to zinc [13,16,24,25,26,29,30,31]. Likewise, the inhibitory action of preventive OP protection has also been shown against chemical carcinogenesis induced by NMU in rats [Paper in progress].

Admittedly, a crucial objection which may be raised concerns the possible inhibition of destructive effects on neoplasic cells caused by protective oligoelements. This issue has been dealt with by numerous authors, to reach the conclusion that the antineoplasic activity of chemotherapy is not significantly affected [11,12,13,14]. Though somewhat paradoxical, this phenomenon is partly explained by the diverse sensitivity towards oligoelements displayed by transformed as compared to normal cells. As already pointed out, selenium is incapable of protecting atypical cells in vitro against antineoplasic drugs [13] and zinc exhibits a similar behavior [15,16]. It is also likely that oligoelements may exert a different effect on neoplasic versus normal cells mainly because of subsequent metabolic changes during cell transformation. Thus, it has been found that in vitro selenium exerts opposite effects on cAMP metabolism, in the presence of murine hepatoma cells or normal hepatocytes, with the former undergoing a marked increase in cAMP [41,42]. Such effects leading to growth inhibition of atypical cells [43] are probably due to differences in phosphodiesterases present in either cell type.

Bearing in mind the peculiar blood supply features of metastasic microspheres, it may be conjectured that the poorly irrigated center of the tumoral mass is free of the penetration of chemotherapeutic agents up to quiescent cells [7,44,45]. Instead, the possibility of trebling the therapeutic dose would allow increasing the concentration gradient at the tumoral border, thus favoring penetration up to the center of microspheres.

In the present study we have clearly established the protective effect of treatment with phospholipases and oligoelements on normal rats receiving large doses of chemotherapeutic agents. Previously, we had shown the therapeutical effect of this combination on animals with experimentally-induced mammary tumors [43], as well as the preventive action on carcinogenesis [44]. In a further stage, it is therefore essential to carry out a combined study with chemotherapeutic agents on animals with experimental tumors, which will enable the confirmed protective action to be evaluated and determine whether the proposed medication positively modifies the antineoplasic effect of chemotherapy.

Overall, our results show improved tolerance to the toxic effects of the chemotherapeutic drugs assayed, by means of combined treatment with phospholipase $A_2$ and oligoelements. Such low-cost medication, lacking any deleterious collateral effects and having confirmed immunostimulating and antineoplasic activity, thus represents a useful clinical tool.

To sum up, the present studies on tolerance to cytostatic drugs by male Spragüe-Dawley rats allow the following conclusions to be drawn:

Animals injected intraperitoneally with CMF (cyclophosphamide, methotrexate, 5-fluoruracil), in doses equivalent to those received by human patients with mammary tumor (cyclophosphamide 500 $mg/m^2$, methotrexate 40 $mg/m^2$ and 5-fluoruracil 600 $mg/m^2$), showed a drop in body weight as from the day following administration of the combined drugs, and proving more marked as a greater CMF dose was employed.

Toxic macroscopic effects became evident as the assayed dose was increased, as a multiple of the basic dose indicated above. At doses greater than 10-fold the basic dose, nasal and gut hemorrhage appeared to a diverse degree starting on the day after CMF administration, correlating closely with the dose. As from the 10-fold dose there was also an obvious increasingly brownish fur coloration, whose degree likewise correlated with the CMF dose.

Animals protected with OP (oligoelements plus phospholipase $A_2$) presented similar features to those already described. However, body weight recovery proved statistically faster in OP-protected rats than in unprotected controls.

CMF proved lethal for unprotected control animals as from the 10-fold dose. The estimated $LD_{50}$ was equivalent to 14.1 times the basic dose.

Such lethal action became evident in rats protected daily with OP medication starting from 14 times the basic dose, the estimated $LD_{50}$ for treated batches being 18.3 times the basic dose.

The anatomopathological findings showed that protected animals suffered significantly less generalized sepsis and medullar aplasia. Also was stated a protective effect on chronic mielloyd leukemia post-chemotherapy in long term survival animals.

These findings imply a better tolerance to the toxic effects of the chemotherapeutic drugs assayed, when supplemented with the combined medication of oligoelements and phospholipase $A_2$, since the $LD_{50}$ increased significantly in protected rats versus unprotected controls. Such correlation provides a valuable therapeutic tool, particularly as the assayed drugs are routinely employed for the treatment of human mammary carcinoma and the doses assayed in the animals are equivalent to those used in oncological medicine.

HUMAN STUDIES

Materials and Methods

In the present work twenty one patients were studied, who underwent hemicholectomy owing to colonic carcinomas, and who since surgery developed liver metastases confirmed by biopsy or by reliable imaging .diagnostic procedures. Metastases could not be treated by surgical methods due to their number, localization, size or poor general condition of the patients. Due to different causes, age, general condition, intolerance or refusal to being treated, none of them received complete chemotherapy. Based on previous reports (1,2,3, 4,5,6,7,8,9,10,11,12), different combinations of zinc, selenium and manganese, with the addition of phospholipase $A_2$, were assayed with tumor cells cultured in vitro. After wards they were tested in rats bearing chemically induced mammary carcinomas with an excellent therapeutic response. The patients were treated with the best combination determined by experimental assays. Because of the good evolution observed, the treatment continued for diverse periods, up to 36 months, and six complete remissions, five partial remissions, stabilization in six cases and progression in four were recorded. In all such cases the common feature was an excellent survival condition.

In order to investigate whether oligoelements and phospholipase $A_2$ may exert a modulatory action on tumor cell growth and proliferation, in vitro studies were performed employing the clonogenic agar technique which allows differential growth of transformed cells.

Tumor induction

Tumors were obtained by intraperitonal (i.p.) injection of three 50 mg/kg doses of N-nitroso-N-methylurea (NMU) to inbred Sprague-Dawley female rats, aged 50, 80 and 110 days, as described previously (12,40,41,42). Neoplasms were histopathologically classified as mammary duct carcinomas.

Tumors for in vitro experiments were surgically obtained during the exponential growth phase having a diameter no greater than 2 cm.

Cellular suspension

Tumor specimens were carefully trimmed and cut into 1-2 mm pieces, washed twice and digested enzymatically at 37° C. for 20 min with pronase-DNAse.

The supernatant of the digestion was carefully extracted and centrifuged at 1000 rpm for 3 min. The cellular pellet was washed three times with Hanks' solution and then resuspended in tissue culture medium to a final concentration of $2\times10^6$ cells/ml. Viability was assessed by Trypan blue dye exclusion test.

Cell culture technique

The method employed was the clonogenic agar technique.

A single cell suspension from tumoral tissue was cultured in soft agar under serum free medium conditions. Approximately 4-5×105 cells were plated per well. The bottom layer consisted of McCoys' A medium, adequately enriched with a final agar concentration of 0.5%. The upper layer contained the the cellular suspension and 0.3% of agar.

Multiwells were incubated at 37° C. in an humidified atmosphere of 5% of $CO_2$ in air. The number of colonies on day 21 after plating was the parameter used to evaluate the mitogenic or inhibitory effect of the different drugs.

Treatments tested in vitro

The three various oligoelements (Mn, Se and Zn) were tested adding 20 µl of each dilution per well.

Dose-response curves were traced with each point run in quadruplicate. Results were expressed as percentage of inhibition calculated as the relation between the number of colonies developed for each treatment and the number of colonies in the control well.

Tested treatments were as follows:

Combination of differentoligoelements at different concentrations.

Combination of oligoelements plus phospholipase $A_2$ at different concentrations.

Combination of oligoelements at the most effective dilutions plus phospholipase $A_2$ at different concentrations.

Patients

Patients were selected taking into account their exclusion from other therapeutic schedules, whether surgical due to the multiplicity of liver metastases, chemotherapeutic because of age, general condition, intolerance or rejection of treatment. These criteria were followed in order to ensure the greatest reliability in the analysis of results. Twelve of the patients (57%) were males, whose ages ranged from 60 to 84 years with a mean value of 69.5 years (Table 1).

Out of the 21 selected patients, only three had previously received a single, incomplete, chemotherapeutic cycle and all discontinued treatment after the first dose because of intolerance or by personal decision. Moreover, chemotherapy had been given at least one year before inclusion/admision: on.

Patients with clinical evidence of disease progression or with an increase in oncological marker serum levels, were not excluded from this study.

Ten of the patients presented a diagnosis of metastatic disease at baseline (Table 1). A further six developed metastases during the first year of illness and the remainder, one year later. Eighty percent of the patients were in Duke's C or D stage at the time of diagnosis of the primitive tumor, 15% were in B stage and 5% in D stage.

In eight patients liver metastases were confirmed by biopsy and in the remainder on the basis of repeated and progressive imaging studies of diverse complexity. All treated patients had histological confirmation of the primitive tumor. Most cases corresponded to moderately differentiated adenocarcinomas (43%, Table 2); 15% were classified as well differentiated, with only one case scarcely differentiated, while the remainder failed to exhibit recognizable typification.

In twelve cases metastasis localization was diffuse, while in the remainder foci were located in the right hepatic lobe (Table 1). Only three of the patients had undergone surgery one year before starting the treatment, but by the time they entered this trial, they were in relapse and the disease was in progression.

Metastasis size ranged from 2 cm, in cases of multiple secondary lesions, to a maximum of 15 cm in patients with greater progression; while the mean value was 5.5 cm (Table 1)

Results obtained showed that the combination of oligoelements led to a significant dose-dependent inhibition of cell proliferation.

Maximal inhibition was produced by dilutions lower than $10^{-3}$ of the main solution and reached 60%; $ED_{50}$ was $10^{-4}$ (FIG. 1).

Independently, phospholipase $A_2$ presented a dose-dependent antagonic behaviour. At dilutions lower than $10^{-5}$, it produced a slight inhibition in the formation of colonies, while at concentrations bigger than to $10^{-6}$ it showed a stimulating effect on cellular proliferation. Combined treatment with oligoelements and phospholipase showed similar inhibitory effects to the one produced by oligoelements alone.

Figure 3:
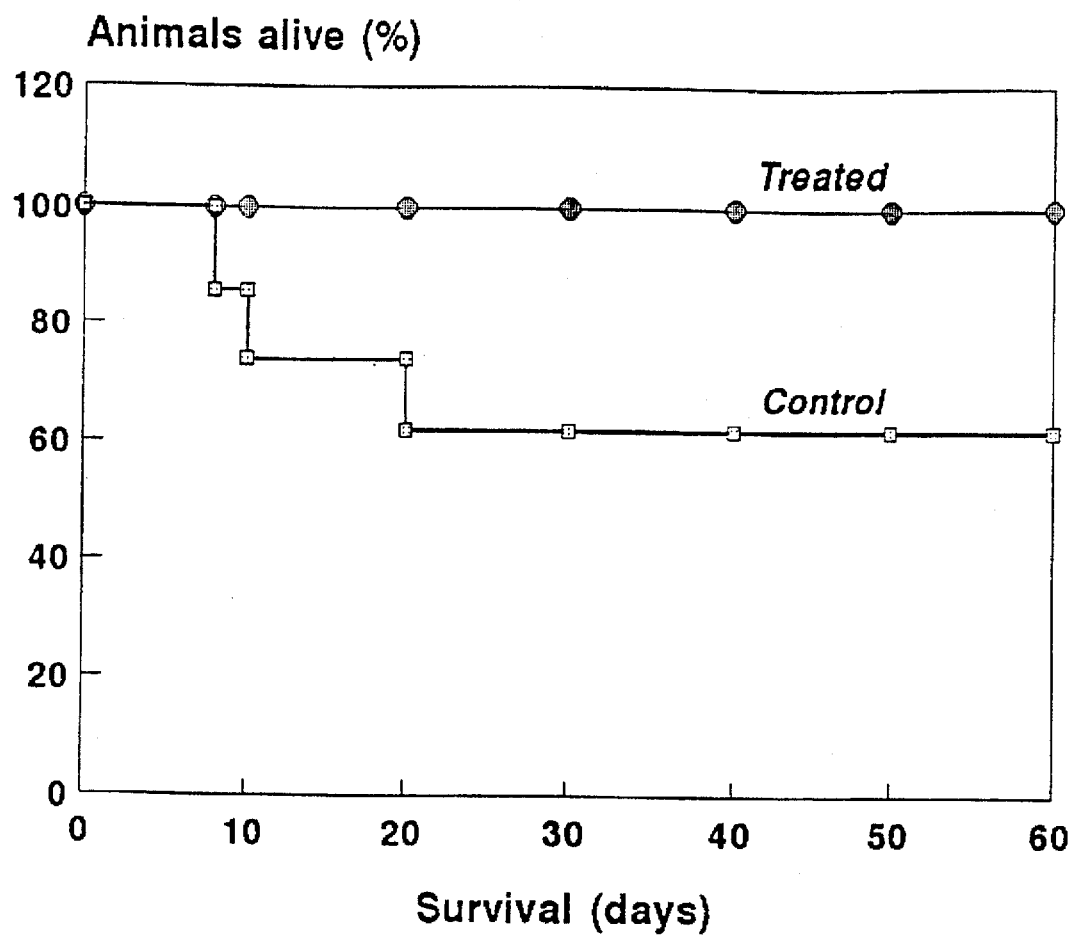
FIG. 3. Survival of animals treated with a 14-fold CMF dose (control) [basic dose: cyclophosphamide 500 mg/m$^2$, methotrexate 40 mg/m$^2$ and 5-fluomracil 600 mg/m$^2$]. While rats treated presented no deaths, mortality approached 40% in controls (P<0.064, Wilcoxon test).
Figure 4:
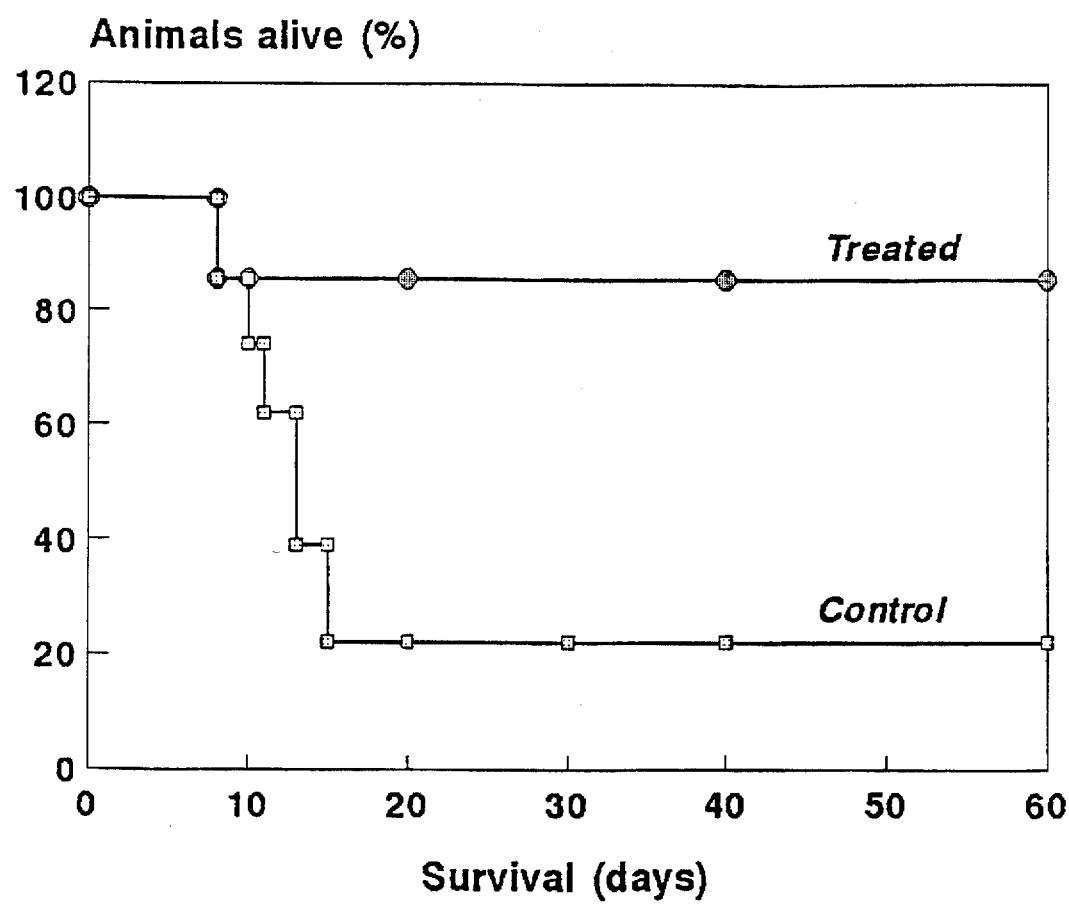
FIG. 4. Survival of animals treated with a 16-fold CMF dose (basic dose: cyclophosphamide 500 mg/m$^2$, methotrexate 40 mg/m$^2$ and 5-fluoruracil 600 mg/m$^2$). While rats treated with micronutrients presented 10% deaths, controls showed over 75% mortality (P<0.0052, Wilcoxon test).
Figure 5:
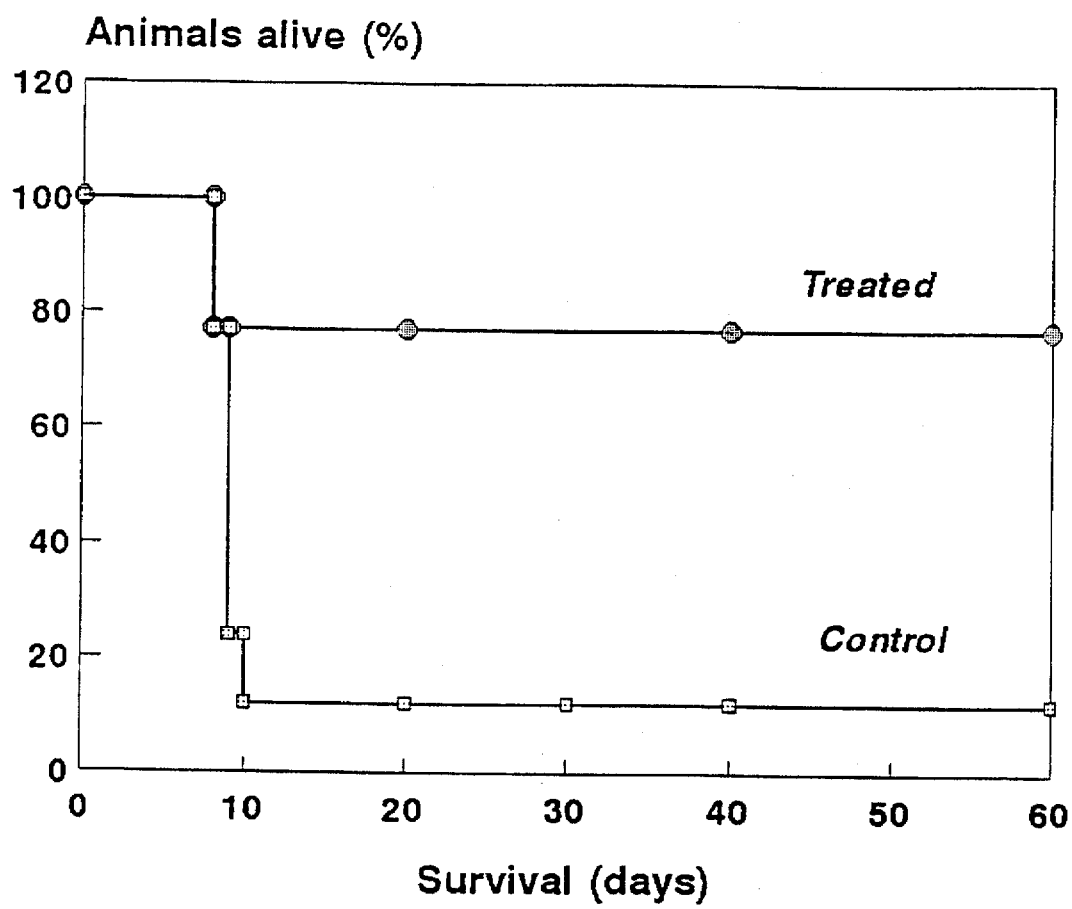
FIG. 5. Survival of rats treated with an 18-fold CMF dose (basic dose: cyclophosphamide 500 mg/m$^2$, methotrexate 40 mg/m$^2$ and 5-fluoruracil 600 mg/m$^2$). The difference in mortality between animal groups is enhanced: 20% for those receiving OP treated versus 88.5% for controls (P<0.0023, Wilcoxon test).
Figure 6:
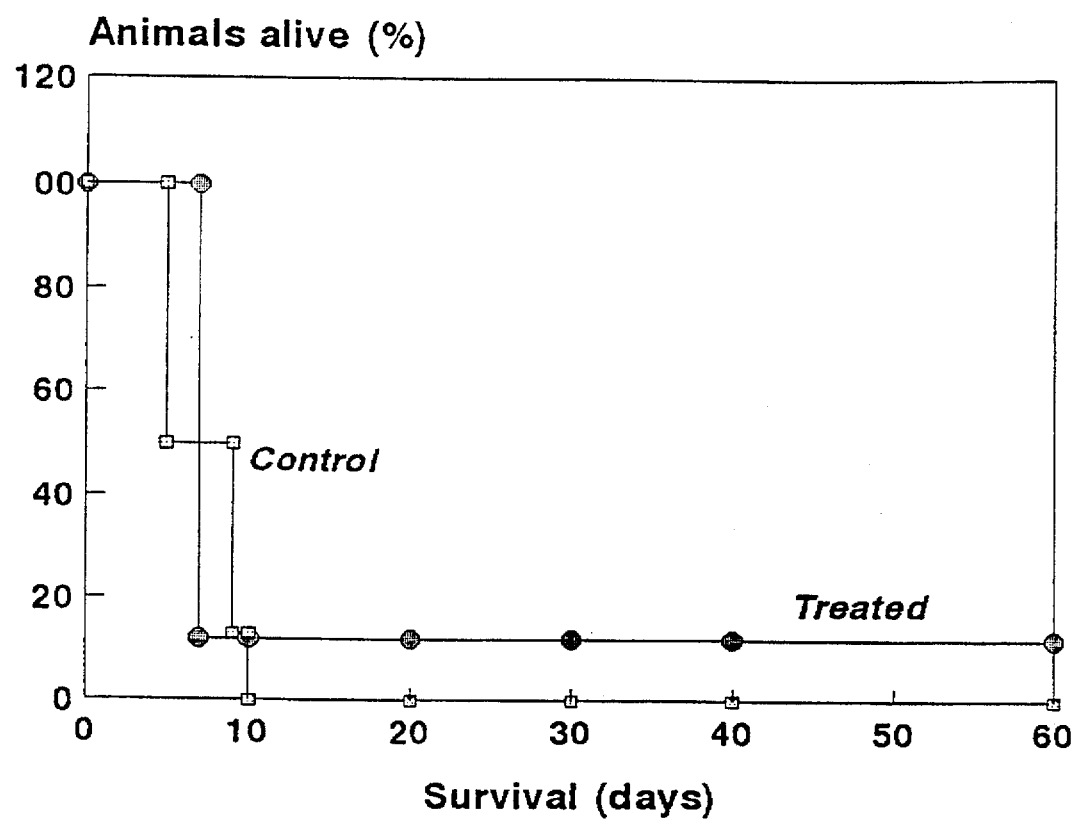
FIG. 6. Survival of animals treated with a 20-fold CMF dose. Controls showed 100% mortality and only 10% of rats receiving OP protection survived at 60 days post-CMF despite the high dose applied (P=NS).
Figure 7:
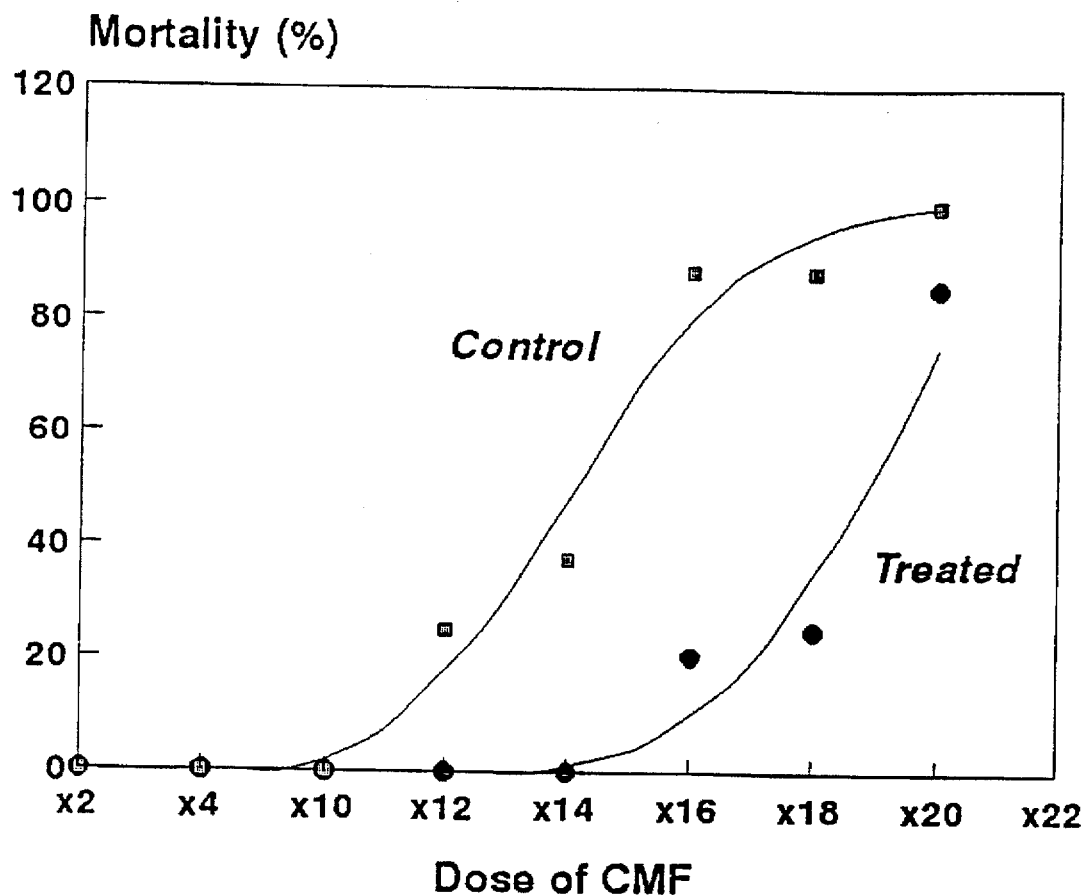
FIG. 7. Lethal Dose 50 in rats receiving CMF alone versus those also treated with micronutrients Mn-Se-Zn and phosholipase $A_2$. (14.1 vs. 18.3 times the basic dose)

A dose dependent inhibition was observed with a maximum of 60% as from the $10^{-5}$ dilutions and with ED50 at the $10^{-4}$ dilution (FIG. 3).

The combination of oligoelements in inhibitory concentrations with phospholipase in stimulating dilutions showed growth inhibition slightly greater than the combination of both in equal concentrations (FIG. 3).

These results allowed to extrapolate the corresponding dose for the treatment of Sprague-Dawley rats with mammary NMU-induced carcinomas, obtaining excellent results with a significant rise in survival rate (12).

These doses agreed with the ones applied by other authors in in vitro studies with Zn and Se to evaluate the protective differential effect on normal cells produced by these elements before treatment with alkaline agents (3)(8).

The treatment of Sprague-Dawley rats with this combination of phospholipase and oligoelements initiated prior to the administration of carcinogen produces a significant decrease (80%) in the development of mammary tumors (unpublished data). Similar effects on carcinogenesis inhibition have been reported for Se (2)(5)(10).

Toxicity studies on Spague-Dawley rats applying 10, 100 and 500 times the therapeutic dose for a prolonged time evidenced neither toxicity nor variations in the survival rate of the animals. Besides, no morphological lesions were found at necropsy autopsy (12). Other authors have described similar results in toxicity studies with Se (7) and Zn (45). For the treatment of human patients, 1.5 µg/kg daily doses of Zn, Se and Mn were given together with 0.10 ug/kg of phospholipase $A_2$ by parenteral and sublingual routes. These doses were obtained by extrapolation of in vitro studies on cellular cultures and in vivo studies on experimental tumors.

Treatment of human patients

In all twenty one patients included in this protocol, great improvement in survival was observed with a mean time of 35±19 months from the initiation of treatment with phospholipase and oligoelements. One or more hepatic metastases were already present in 95% of the cases at the time of the starting treatment.

Moreover, we recorded a mean survival of 69.6±30 months from the date of diagnosis of the primitive tumor.

At the time of analysing presented results, all patients were alive, having been admitted to the protocol after the detection of hepatic metastasis in 95% of cases (Table 3). The main criteria on for patient selection was their exclusion from other therapeutic approaches.

In 80% of cases treated patients were classified as Dukes C or D (Stage 1).

The general condition of the patients remarkably improved by the treatment with a normalization of humoral parameters in many cases, while oncological markers became negative, and pain disappeared (Table 3). Patients failed to present signs of intrahepatic bile duct obstruction or signs of liver failure in spite of hepatic metastasis extension and its multiplicity in some cases. No signs of toxicity were observed due to medication components. Neither were there any complications due to intramuscular parenteral administration in spite of the need of daily administration during long periods (up to 49 months).

To date, all patients are alive. Nine of them are in very good general condition; nine in good condition and the other three in poor condition due to the aggravation of pathologies unrelated to hepatic metastasis.

Remissions were complete in six cases, partial in five, remaining stable in six and progression was observed in four.

In a review of world literature we have not found a single case of colon adenocarcinoma with hepatic metastasis presenting spontaneous regression. Scarce cases only occur in clear renal cell carcinomas, neuroblastomas, malignant melanoma, and chorioncarcinoma (45) (47) (48) (49) (50).

This phenomenon is also observed in congenital leukemia associated to Down Syndrome type alterations and other chromosomic aberrations (51)(52)(53), but has not been described in other ontological entities. Due to this, believe that the ten cases presented in this study do not correspond to spontaneous regression but to a response to applied therapeutics. On the other hand, in cases of chemotherapy-treated hepatic metastasis, results are very poor. For instance, with 5-Fluroracyl as a single therapeutic agent, a response of approximately 20% is achieved without improving survival time (54)(55). By supplementing 5-Fluroracyl with leukovorine, which inhibits thymidilate synthetase allowing a major inhibition of DNA synthesis by 5-Fluroracyl (56)(57), improved response rates are obtained but survival rates are not modified significantly (58).

The use of chemotherapic agents in high doses, for example Melphalan (120 mg/m), following leukopoiesis stimulants, such as GM-CSF for bone marrow rescue, has resulted in a response of 33% with a duration of only 2 or 3 months (59). In a series of treated patients, compiled by Moertel, mean survival was estimated to be 5.5 months (60)(61) from the time of liver involvement diagnosis. These data are consistent with other authors estimating mean survival rate to be roughly 6 months, and in two months in the case of alkaline phosphatase increase (advanced disease marker) (62).

The most encouraging studies with 5-Fluroracyl perfusion directly in to the hepatic artery showed that survival could not be extended beyond 10 to 11 months, with 20 to 40% of morbility due to the method (63).

Hepatectomy for colon adenocarcinoma hepatic metastasis is a well-known method. The first intervention of this kind was reported by Garre in 1888 (64).

In some selected cases it improves survival remarkably. However it is only indicated in cases where one hepatic lobule presents at most three lesions (65). In these cases, 36% survival is achieved after a 5-year term, especially in patients with a single metastasis (66)(67)(68). In large series of thousands of patients it has been shown that only 5% of the total cases belong to this category. Hepatic metastasis resections can only improve survival in roughly 1 or 2% of cases (65).

In our series of patients only one had been selected for hepatectomy. At the initiation of treatment that patient was in relapse. Surgical methods in the above conditions may eradicate the disease and extend survival periods substantially. Unfortunately, this method cannot be applied in all cases. When multiple metastasic lesions appear together with bilobular involvement, adverse physical conditions of patients and signs of terminal disease (hepatomegaly, ascites, high alkaline phosphotase and liver failure, among others), chemotherapy has not proven to be an adequate substitute to surgery as regards longer survival. Therefore, it seems highly encouraging to obtain a mean survival time of 35 month from the start of the treatment with phospholipase and oligoelements in patients excluded from other protocols and free from any other treatment. Although we are not proposing our method as an alternative to others, we believe it is indeed useful in the above cases. It is also applicable as a treatment complementary to hepatectomy and conventional chemotherapy since we have already improved the results of this latter procedure (35 months versus 11 months of survival) without toxic or undesirable effects.

The mechanisms of action through which our combined phospholipase-oligoelements treatment exerts its therapeutic effect are most likely multiple in nature. The marked response obtained in cellular cultures, in a dose-dependent pattern, indicates the existence of direct inhibition mechanisms of cellular proliferation not mediated by the inmune system. A review of the data accumulated for this purpose on cell differentiation systems and apoptosis has led us to propose independent explanations.

Phospholipase-oligoelements treatment apparently affects the cellular capacity of synthesis repair and expression of DNA chains, probably because oligoelements, whether separately or combined are able to influence some of the enzymes involved in the physiological repair of mutated chains. Data supporting this mechanism can be obtained from experimental studies on carcinogenesis. Accordingly, Nickel (Ni) in combination with the peptide glycil-glycil-histidine produces the generation of free oxygen radicals from $H_2O_2$, which acting in the proximity of DNA chains can induce double linkages in cytocine-cytocine and thymidine-thymidine tandems with mutagenic effects (69) (70). This action may be inhibited or reverted by superoxide dismutase, an enzyme that eliminates the superoxide anion and which is located either in the mitochondrion, where it needs Mn for its action, or in the cytosol, requiring Cu and Zn as catalysts (71)(72). Eukariotic cells are protected from $H_2O_2$ by the catalase and the glutathion peroxidase present in both cytosol and mitochondrion (73), the latter having Se as catalyst.

Superoxide dismutase are increases in rats treated with an excess of Se in their diet to prevent carcinogenesis induced by diverse agents as NMU and dimethylhydrazine, among others.(5)(7)(9).

This enzyme is considered responsible at least partially for the benefical effect of Se. Elimination of $O_2$ and $H_2O_2$ is essential since these components in the presence of Fe react releasing hidroxyl radicals (OH) against which no cellular mechanism exists. The latter are capable of oxidizing any biological molecule (membrane lipids, cellular proteins and nucleic acids).

Damage to the suppressor genes as P53 (17P) and DDC (18Q), which, due to their presence in only one of the allels (loss of heterocygotia), or mutated in both allels, or in the remaining allels, or the deleted ones, cause the loss of their regulatory function over cellular proliferation and differentiation (74)(75)(76)(77).

It may be assumed that the favourable action of the oligoelements on the reparair of the damaged gene repair can restitute the atypical cells to the normal circuit, making them return to normal differentiation and apoptosis (programmed cell death). This mechanism has been proposed by Tobey and by Samson and Schwartz in relation to the action of Zn as an inducer of cellular resistance against alkylating agents and their mutagenicity (3)(9)(78). A review of the preventive and reparative mechanisms of the mutagenic effects of $O_2$, $H_2O_2$ and OH groups, include the three elements employed here, Se, Zn and Mn, as essential catalysts of the critical enzymatic steps of the protective process. Their administration in minimal excess and the improvement of their availability through parenteral injection and chemical form are essential facts to explain the remarkable survival differences (both in treated rats and human patients).

However, there are other possible mechanism of action involving a wide range of molecular and immune path ways. For instance, Se has proven to exert an inhibitory effect on the proliferation of atypical cells derived from hepatomas, an effect mediated by the increase in intracellular cAMP due to inhibition of specific phosphodiesterases (30), synergic with that of Mn which in vitro is a direct activator of the adenylyl cyclase. The final result is a marked increase in the cAMP pool. The inhibitory effect on cell proliferation produced by cAMP is widely recognized (79). There is evidence of the releasing effect exerted by phospholipase $A_2$ on histamine and serotonine from mastocytes (80)(81). Under certain conditions, histamine acts by strongly inhibiting cellular proliferation both in vivo and in vitro (40)(82)(83). The presence of histamine receptors in different types of human mammary tumors and melanoma, among others, has been described. (84)(85)(86). In such cases, histamine effects are exerted by H1 receptors increasing cAMP intracellular levels (79). Serotonine acts by the same mechanism, directly and indirectly, through 5HT-1a and 5HT-4 receptors activating adenylyl cyclase with a synergic effect as the above mentioned (87)(88). A scarcely studied effect of serotonine receptors is the stimulation of phospholipase C, with the subsequent increase in phosphatidylinositol hydrolisis and intracellular calcium mobilization (5HT 1c and 5HT 2 receptors). This effect is specifically exerted on hippocampal neurons, cortical entorrinal and fronto-cyngulate sectors (87)(89)(90). The final result of this stimulation is to increase impulse levels from neurons in those cortical areas (91)(92). Some authors attribute this mechanism to 5HT 3 receptors (89). It is worthwhile to correlate these data with previous work on the action of phospholipase-type venoms on cerebral peptides (93). Both mechanisms involving phospholipases and serotonine explain the positive action on appetite and change of attitude towards disease, which were noted in human patients and rats treated with phospholipases and oligoelements. A remarkable property of 5HT-1a receptors is their different activity according to cell differentiation degree. It has been demonstrated that these receptors increase cAMP levels in undifferentiated cells; but they inhibit adenylyl cyclase in well differentiated ones (88). This could explain their different mode of action inhibiting atypical cell proliferation but without affecting normal T lymphocytes. (87)(88).

By ultrastructural immunolabelling, the presence in the mastocyte granules of prostaglandine $E_2$, cyclo-oxygenase and a great pool of phospholipids not arranged in bilayers and forming membrane stuctures, but as an amorphous matrix (81)(94), has been shown.

At the time of granule release these phospholipids form microvesicles when coming in contact with water. Such microvesicles are linked to the granule's membrane and simultaneously to the celt's membrane, thus forming channels that allow exocytosis. Besides, granules contain a great quantity of arachidonic acid (95) which makes them an adequate source to produce eicosanoic acids.

The presence of phospholipases is essential and, since arachidonic acid is usually sterificated in sn-2 phospholipid position, an $A_2$ phopholipase is needed (96), which in turn requires a high concentration of calcium for its action, normally found in the granule. In the case of the mastocyte, the enzyme is situated in the matrix of the granule, unlike the macrophage that possesses it in the membrane (87)(97)(98). As mentioned above, 5HT-2-1c and 5HT-2 serotonine receptors stimulate the increase in intracellular calcium, requirement for phospholipase $A_2$ activation. Therefore, phospholipase $A_2$ causes a feedback circuit which leads to the secretion of mastocyte granules activating in turn the cascade of arachidonic acid through endogenous phospholipase $A_2$ and the pool of granule phosphoinositides. Such pathway precedes PGE2 production by cyclo-oxygenase in the already secreted mastocytes granules (81). It is well known that the effects of the above mentioned components on the cellular micro-environment herald the initiation of inflammatory processes with the subsequent afflux of immunocompetent cells and the necrosis of abnormal tissue components through a specific or non-specific immunomechanism such as T killer lymphocytes and macrophages, culminating in the necrosis of tumoral tissue. Added to growth inhibition of atypical tissues produced by the regulation of intracellular cAMP levels or its metabolizing enzymes, this finding explains at least in theory the results obtained with the medication under study.

A final mechanism suggested for this therapeutic proposal is the necrosis of neoplasic cells mediated by TNF and macrophages.

As early as 1978, Mathwes described the existence of a tumoral necrotizing factor in rabbit monocytes (99)(100). Previously, Carwell in 1975 had reported the appearance of a factor in endotoxine-induced serum producing tumoral necrosis, but without identifying it. It was found that the then so-called TNS needed lysosome integrity as well as membrane phospholipase $A_2$ for its action (101). Later, Mathwes established that cellular damage is initially exerted on mitochondria, also suggesting that cytotoxine required the presence of some metal as its action is inhibited by EDTA, presumably affecting a metaloenzyme cell membrane (102)(103)(104). In 1985 Richards described TNF inhibition by corticoid due to arachidonic acid blockade. Corticoids are supposed to induce a nondialyzable protein called lipomoduline or macrochortine that inhibits phospholipase $A_2$. The presence of O2-free radicalys is also necessary for the action of TNF and the metabolism of arachidonate, an essential stage of the cytolitie process(100). Confirming the necessity of phospholipase $A_2$ for TNF action, Mutch in 1992 established that the resistance of some cell lines derived from gynecological tumors to necrosis by TNF is due to the production by these cells of a protein that prevents the activation of the above enzyme (104).

Mechanisms initiated by TNF are not only destructive. Some authors have described its effects on the production of lymphokines in lymphocytes and in macrophages (CSF-1, MCP; monocyte chemoatratan protein 1) and the expression of several genes such as NFK8 which then stimulate several lymphokines and adhesive molecules that play an active role in tissue defense, inflammation and remodelation processes (105)(106)(107)(108)(109). However, the main action of TNF is still exerted as a result of the stimuli by diverse lymphokines such as I12, enhancing the production of gamma IFN in T lymphocytes (110), or I14, also stimulating gamma IFN and requiring macrophages to exert the suppressor effect on mouse tumors. This inhibition is carried out by means of ARNm stimulation for I15, IFN gamma and TNF T lymphocytes(111)(112). The above effects are important to disclose the origin of chronic inflammatory processes and immune induced inflammation.

It may therefore be concluded that the addition of the final effector enzyme of all these mechanisms (phospholipase $A_2$) by a direct route (parenteral) may in some way trigger the above inflammatory processes by offering an effector for the action of alpha TNF. Arachidonic acid is produced from membrane phospholipids leading to the release of $O_2$-free radicals and the production of prostaglandines by cyclooxygenase and other enzymes (81)(109).

It is worthwhile stressing that when performing the analysis of these results (March, 1994), all patients were alive. Nine of them were in a very good general condition; nine in good condition and the other three were in poor condition due to aggravation of pathologies unrelated to hepatic metastasis.

Remissions were complete in six cases and partial in five, while six remained stable and progression was observed in only four cases, with excellent life quality throughout. We could state that while oligoelements protect normal cells from the effects of oxygen free radicals and may perhaps induce the apoptosis of atypical cells, allowing the repair of their genomic damage, phospholipase $A_2$ promotes the destruction of atypical cells, both in a direct and indirect way. In a direct way, by means of activation of the same mechanisms of cellular destruction inhibited by oligoelements, that is the release of $O_2$ free radicals. In an indirect way, by means of histamine and serotonine release from mastocyte granules and acting as final effector substrate of the effects mediated by gamma INF, I12, I14 and TNF already present in the tumoral microenvironment. Finally, the afflux of immuncompetent cells and macrophages to the site of development of the destructive processes may produce feedback of the mentioned mechanisms.

It might seem contradictory to support the fact that the action of the two groups of compounds utilized is antagonic. Nevertheless, it has been reported that oligoelements exert entirely different effects on atypical cells as compared with normal ones. For instance, it has been demonstrated that normal cell culture pretreatment with Zn, Cu and Se makes it 16 times more resistant to high doses of Melaphalan than untreated cultures. On the other hand, atypical cell cultures show scarce (30%) or null improvement of resistance to alkylating agents(8).

Consequently, we believe that the previously discussed hypothesis, provides a valid explanation for the therapeutic basis of our treatment. Since the mechanism of action is non-specific, it may be applied to several neoplasic pathologies and, hence, to a wide range of patients. It is also evident that possible modifications of oncogen and oncoprotein expressions, as well as the capacity to induce apoptosis promoted by the application of phospholipase and oligoelements must be further investigated in cellular cultures.

TABLE 1

| Patient # | Primitive Tumor Diagnosis | Hepatic Metastasis Diagnosis | Metastasis Size | Hepatic Metastasis Location | Hepatic Metastasis Sugery | Chemotherapy |
| --- | --- | --- | --- | --- | --- | --- |
| 1 | 04-14-86 | 05-08-86 | Multiple Centimet. | Diffused | N/A | N/A |
| 2 | 12-15-89 | 07-30-91 | 6. 2.5 and 2 cm. | right and left lobules | N/A | N/A |
| 3 | 11-14-89 | 09-08-89 post-surg. 05-08-91 | 8 cm. then 8 cm. 2 cm. | right lobule | hepatectom 11-17-89 rec. 5-8-91 | N/A |
| 4 | 09-04-90 | 11-05-92 | 3 cm. | right lobule | N/A | N/A |
| 5 | 01-20-91 | 01-25-91 | 4 cm. 7 cm. | segments 4 and 5 | N/A | N/A |
| 6 | 11-25-91 | 11-28-91 | 3 cm. 4 cm. 7 cm. | right lobule | N/A | N/A |
| 7 | 11-07-92 | 01-07-92 | 7 cm. 8 cm. | multiple diffused | N/A | N/A |
| 8 | 10-16-90 | 10-29-90 | multiple centimet. | multiple diffused | N/A | N/A |
| 9 | 05-13-91 | 11-03-91 | 8 cm. | segment 8 | N/A | Single dose no tolerance |
| 10 | 09-14-90 | 07-15-91 | 5 cm. | right lobule | N/A | N/A |

TABLE 2

| PATIENT # | Primite Tumor Diagnosis | Hepatic Metastasic Diagnosis | Metastasis Size | Hepatic Metastasic Location | Hepatic Metastasic Surgery | Chemotherapy |
|---|---|---|---|---|---|---|
| 11 | 2-10-89 | 1-9-91 | 1 Cm. | Caudal Lobe | No | No |
| 12 | 1-4-90 | 2-9-91 | Centimetric | Multiple Difused | No | No |
| 13 | 8-11-92 | 8-27-92 | 15 Cm. | Hepatic Dome Multiple | No | No |
| 14 | 3-26-92 | 3-26-92 | 3 Cm. And 3.2 Cm. | Right Lobe | No | No |
| 15 | 2-15-92 | 2-15-92 | Centimetric | Multiple | No | Discontinued After Hepatic Artery Trombosis |
| 16 | 1-14-92 | 2-14-92 | 3 To 4 Cm. | Multiple | No | No |
| 17 | 8-16-91 | 8-16-91 | Centimetric | Left Lobe Multiple | No | No |
| 18 | 11-26-86 | 3-9-91 | Centrimetric | Residual Right Lobe 3-9-90 | Heptatectomy 6-26-90 | No |
| 19 | 12-15-78 1-25-86 10-15-86 | 2-17-90 | 1 Cm. | Residual Left Lobe 2-17-90 | Hepatectomy 1-23-89 | No |
| 20 | 5-2-91 | 10-15-91 | 1 Cm. And 0.92 Cm. | Right Lobe | No | No |
| 21 | 1-10-92 | 3-11-92 | Until 3 Cm. | Multiple Difused | No | No |

TABLE 3

| Patient # | Sex | Age (in yrs.) | Histological Type | Dukes Grade | H.M. Diagnosis Method |
|---|---|---|---|---|---|
| 1 | Female | 72 | Semidiff. Adenocar. | C | Hepatic Biopsy |
| 2 | Male | 65 | Infiltranting differen. Adenocar. | B | Repeated Image methods |
| 3 | Male | 80 | Well differentiated Adenocar. | C | Biopsy and hepatectomy |
| 4 | Male | 80 | Moderately differentiated Adenocar. | B | Repeated Image methods |
| 5 | Male | 66 | Adenocar. | C | Repeated Image methods |
| 6 | Male | 70 | Adenocar. | C | Biopsy, Hepatic cuneus |
| 7 | Female | 60 | Infiltrating Adenocar. | C | Biopsy, Hepatic cuneus |
| 8 | Female | 67 | Differentiated Adenocar. | C | Repeated Image methods |
| 9 | Female | 68 | Differentiated Adencar. | C | Repeated Image methods |
| 10 | male | 67 | Well differ. Adenocar. | C | Repeated Image methods |

TABLE 4

| Patient # | Sex | Age (in yrs.) | Histological Type | Dukes Grade | H.M. Diagnosis Method |
|---|---|---|---|---|---|
| 11 | Female | 80 | Semi-differentiated Adenocarcinoma | C | Repeated Image methods |
| 12 | Female | 67 | Well-differentiated Adenocarcinoma | C | Repeated Image methods |
| 13 | Female | 61 | Semi-differentiated Adenocarcinoma | C | Intraoperatorial Observatory and image methods |
| 14 | Female | 73 | Scarcely-differentiated Adenocarcinoma | D | Intraoperatorial Observatory and image methods |
| 15 | Male | 74 | Semi-differentiated Adenocarcinoma | C | Intraoperatorial Observatory and image methods |
| 16 | Male | 72 | Semi-differentiated Adenocarcinoma | C | Repeated Image methods |
| 17 | Female | 64 | Semi-differentiated Adenocarcinoma | B | Introperatorial Observatory and image methods |
| 18 | Male | 57 | Semi-differentiated Adenocarcinoma | C | Repeated Image methods |
| 19 | Male | 67 | Adencarcinoma | C | Repeated Image methods |
| 20 | Male | 84 | Well-differentiated Adenocarcinoma | C | Repeated Image methods |
| 21 | Male | 68 | Semi-differentiated Adenocarcinoma | C | Repeated Image methods |

TABLE 5

| Patient # | Survival from treatment initiation | Survival from primitive tumor diagnosis | Grade of remission | General Status | Karnofsky |
|---|---|---|---|---|---|
| 1 | 94 months | 96 months | Complete | Excellent | 100 |
| 2 | 29 months | 50 months | Stable | Very good | 90 |
| 3 | 27 months | 127 months | Complete | Very good | 100 |
| 4 | 37 months | 44 months | Complete | Poor (hemiplegia) | 40 |
| 5 | 33 months | 37 months | Partial | Poor (uremia) | 50 |
| 6 | 26 months | 33 months | Partial | Good | 70 |
| 7 | 23 months | 25 months | Stable | Good | 70 |
| 8 | 39 months | 46 months | Complete | Very good | 100 |
| 9 | 22 months | 33 months | Progressive | Fair | 60 |
| 10 | 39 months | 43 months | Stable | Very good | 80 |

TABLE 6

| Patient # | Survival from treatment initiation | Survival from primitive tumor diagnosis | Grade of remission | General Status | Karnofsky |
|---|---|---|---|---|---|
| 11 | 38 months | 56 months | Complete | Good | 80 |
| 12 | 37 Months | 50 months | Stable | Very Good | 90 |
| 13 | 19 Months | 19 months | Stable | Very Good | 90 |
| 14 | 24 Months | 24 months | Progression | Regular | 60 |
| 15 | 25 Months | 25 months | Partial Remission | Very Good | 100 |
| 16 | 25 Months | 26 months | Progression | Good | 80 |
| 17 | 31 Months | 31 months | Partial Regerssion | Very Good | 90 |
| 18 | 36 Months | 45 months | Stable | Very Good | 90 |
| 19 | 49 Months | 90 months | Complete Remision | Very Good | 100 |
| 20 | 27 Months | 36 months | Partial Remission | Good | 80 |
| 21 | 24 Months | 26 months | Progression | Good | 80 |

The invention has been described with reference to various specific and preferred embodiments and techniques. However, it should be understood that many variations and modifications may be made while remaining within the spirit and scope of the invention.

What is claimed is:

1. An immuno-enhancer composition comprising a solution of at least one oligoelement selected from the group consisting of sodium selenite, magnesium chloride, manganese chloride, zinc chloride, cobalt, cerium, molybdenum, and silicon; and phospholipase A2, wherein said composition is prepared by mixing aliquots of a solution of said oligoelement in distilled water and a solution of phospholipase A2 in a sodium phosphate buffer.

2. The method of preparing an immuno-enhancer composition comprising a solution of at least one oligoelement selected from the group consisting of sodium selenite, magnesium chloride, manganese chloride, zinc chloride, cobalt, cerium, molybdenum, and silicon; and phospholipase A2 comprising the steps of preparing a solution of the oligoelement by the oligoelement in distilled water;

preparing a solution of phospholipase A2 in a sodium phosphate buffer; and preparing the composition by mixing aliquots of the oligoelement solution and the phospholipase A2 solution.

* * * * *

UNITED STATES PATENT AND TRADEMARK OFFICE
CERTIFICATE OF CORRECTION

PATENT NO. : 5,698,583
DATED : December 16, 1997
INVENTOR(S) : Dr. Ernesto Crescenti It is certified that error appears in the above-identified patent and that said Letters Patent is hereby corrected as shown below:

In claim 2, line 7, please insert --dissolving-- after "by".

Signed and Sealed this

Twenty-sixth Day of May, 1998

*Attest:*

BRUCE LEHMAN

*Attesting Officer*         *Commissioner of Patents and Trademarks*